US011276166B2

(12) United States Patent
Prasad et al.

(10) Patent No.: US 11,276,166 B2
(45) Date of Patent: Mar. 15, 2022

(54) SYSTEMS AND METHODS FOR PATIENT STRUCTURE ESTIMATION DURING MEDICAL IMAGING

(71) Applicant: GE Precision Healthcare LLC, Milwaukee, WI (US)

(72) Inventors: Raghu Prasad, Bangalore (IN); Yu Huang, Beijing (CN); Yanran Xu, Beijing (CN); Kiran Panchal, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 164 days.

(21) Appl. No.: 16/730,694

(22) Filed: Dec. 30, 2019

(65) Prior Publication Data

US 2021/0201476 A1 Jul. 1, 2021

(51) Int. Cl.

| | |
|---|---|
| ***G06K 9/00*** | (2006.01) |
| ***G06T 7/00*** | (2017.01) |
| ***G06T 7/44*** | (2017.01) |
| ***G06T 7/10*** | (2017.01) |
| ***G06T 7/50*** | (2017.01) |
| ***A61B 6/04*** | (2006.01) |
| ***G06K 9/46*** | (2006.01) |

(52) U.S. Cl.

CPC .......... *G06T 7/0012* (2013.01); *A61B 6/0407* (2013.01); *G06K 9/4642* (2013.01); *G06T 7/10* (2017.01); *G06T 7/44* (2017.01); *G06T 7/50* (2017.01); *G06T 2200/04* (2013.01); *G06T 2207/10024* (2013.01); *G06T 2207/10028* (2013.01); *G06T 2207/10072* (2013.01); *G06T 2207/10144* (2013.01); *G06T 2207/10152* (2013.01)

(58) Field of Classification Search

None

See application file for complete search history.

(56) References Cited

U.S. PATENT DOCUMENTS

| | | | | |
|---|---|---|---|---|
| 7,869,562 | B2 | 1/2011 | Khamene et al. | |
| 9,811,902 | B2 | 11/2017 | Flohr et al. | |
| 9,900,584 | B2 | 2/2018 | Nisenzon | |
| 10,097,793 | B2 | 10/2018 | Eldar et al. | |
| 10,163,195 | B2 | 12/2018 | Berlin et al. | |
| 10,331,850 | B2 | 6/2019 | Singh et al. | |
| 2010/0033604 | A1 * | 2/2010 | Solomon | H04N 5/2253 348/241 |
| 2013/0009955 | A1 * | 1/2013 | Woo | G06T 5/005 345/419 |
| 2015/0213646 | A1 | 7/2015 | Ma et al. | |
| 2016/0048958 | A1 * | 2/2016 | Miga | A61B 8/483 382/131 |

(Continued)

FOREIGN PATENT DOCUMENTS

| | | |
|---|---|---|
| CN | 109741405 A | 5/2019 |

*Primary Examiner* — Wei Wen Yang

(74) *Attorney, Agent, or Firm* — McCoy Russell LLP

(57) ABSTRACT

Methods and systems are provided for estimating patient structure prior to a scan by a medical imaging system. As one example, a method may include acquiring depth images of a patient positioned on a table of the medical imaging system, correcting the depth images based on histogram data from the depth images, and extracting a three-dimensional structure of the patient based on the corrected depth images.

20 Claims, 13 Drawing Sheets

(56) References Cited

U.S. PATENT DOCUMENTS

| | | | | |
|---|---|---|---|---|
| 2016/0191887 | A1* | 6/2016 | Casas | A61B 34/20 348/47 |
| 2017/0112460 | A1* | 4/2017 | Merckx | A61B 6/545 |

* cited by examiner 600
606
608
610
622
624
604
602
616
620
618

800

SYSTEMS AND METHODS FOR PATIENT STRUCTURE ESTIMATION DURING MEDICAL IMAGING

FIELD

Embodiments of the subject matter disclosed herein relate to medical imaging systems, and more particularly, to accurate patient structure estimation prior to medical imaging.

BACKGROUND

Non-invasive radiographic imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures). In modern CT imaging systems, a gantry—a circular frame with an x-ray tube on one side and a detector on the other—rotates around a patient positioned on a table, producing several thousand sectional views of the patient in one rotation. For the use of these imaging technologies to be effective, the patient or object must be properly positioned and oriented within the imaging system.

BRIEF DESCRIPTION

In one embodiment, a method for a medical imaging system comprises acquiring depth images of a patient positioned on a table of the medical imaging system, correcting the depth images based on histogram data from the depth images, and extracting a three-dimensional structure of the patient based on the corrected depth images. Thus, loss of depth information due to uneven exposure and holes with an extracted three-dimensional patient structure/avatar/mesh/point cloud may be eliminated. In this way, an accurate estimation of patient structure and orientation may be achieved prior to imaging.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
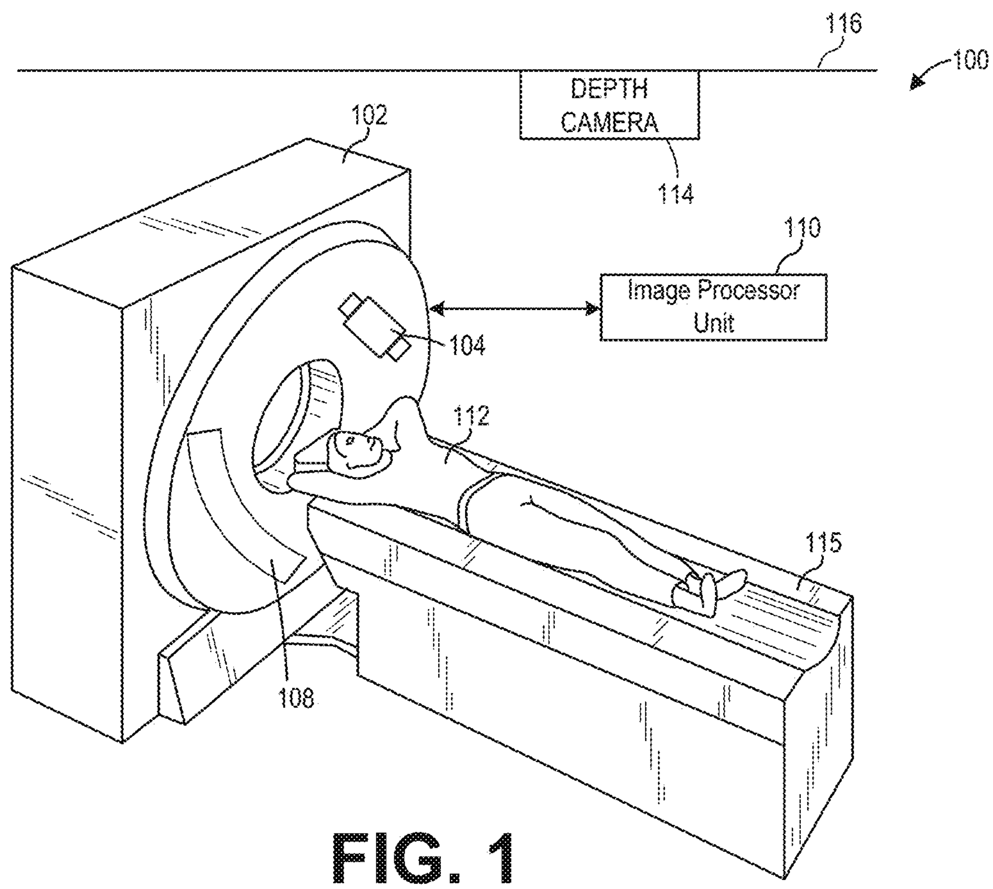
FIG. 1 shows a pictorial view of an imaging system according to an embodiment.

The following description relates to various embodiments of medical imaging systems. In particular, systems and methods are provided for determining an accurate three-dimensional (3D) depth estimation of a patient structure free of illumination, reflection, and exposure artifacts prior to radiological imaging. Patient structure, position, and orientation all affect radiological imaging results. An inappropriate position and/or orientation of the patient during or before the scan may significantly impact both image noise and patient surface dose. As an example, placing the patient off center may result in imaging artifacts and unnecessary radiation exposure to more sensitive regions of the body.

A desired patient position and orientation (e.g., a pose) for a radiological exam is based on a body part to be imaged, a suspected defect or disease, and a condition of the patient, with a protocol for positioning determined by a radiologist. The prescribed protocol is then carried out by a technologist operating the imaging system in order to obtain accurate diagnostic information and reduce x-ray exposure of the patient. Further, the technologist may manually adjust a height and lateral position of a scanning table on which the patient is positioned in order to align the patient for the radiological exam. However, technical errors may be made by the technologist due to, for example, high workloads and an inefficiency of the manual positioning. For example, the technical errors may result in images obtained during the radiological exam having over-exposure, under-exposure, or wrong positioning of the patient. As a result, the radiologist may decide to reject and repeat the scan in order to make an accurate diagnosis. In such examples, an immediate second radiograph may be requested if the patient is available. Alternatively, the patient may have to return for an additional appointment to be re-scanned. Both options increase patient discomfort, patient exposure to radiation, cognitive stress on scan operators, and the amount of time until diagnosis.

Therefore, various techniques have been employed to expedite radiological exam workflows. Among them is the integration of time-of-flight (ToF) or depth cameras into radiological exam rooms. Prior to the radiological imaging, the ToF or depth camera may be used to generate a 3D depth image of the patient. The 3D depth image may be used to determine patient structure, including anatomical landmarks, body contour, body volume/thickness, and patient location/orientation relative to the table. The patient structure may then be compared to positioning parameters set forth by the radiologist. If the determined patient structure is not in alignment with the positioning parameters, the technologist may re-position the patient prior to scanning, thereby decreasing the occurrence of reject and repeat scans.

However, depth cameras still suffer from several sources of noise, such as variable illumination and/or reflective areas present within the exam room. Such noise may result in areas of the 3D depth image lacking depth information, or depth holes. These depth holes may lead to inaccurate patient structure determination, and ultimately, the technologist inaccurately determining if the positioning parameters prescribed by the radiologist are being accurately followed. As a result, reject and repeat scans may continue to occur despite the use of a patient structure estimation prior to scanning.

Thus, according to embodiments disclosed herein, a method and system are provided for identifying and nullifying effects of variable illumination and reflection on depth camera-based estimations of a patient structure. In one embodiment, depth images of a patient positioned on a table of a medical imaging system may be captured, and bracketed exposure depth imaging (BEDI) and/or a coefficient of illumination variation (CoIV)-based correction may be applied to the captured depth images so that an accurate 3D patient structure may be estimated.

Figure 2:
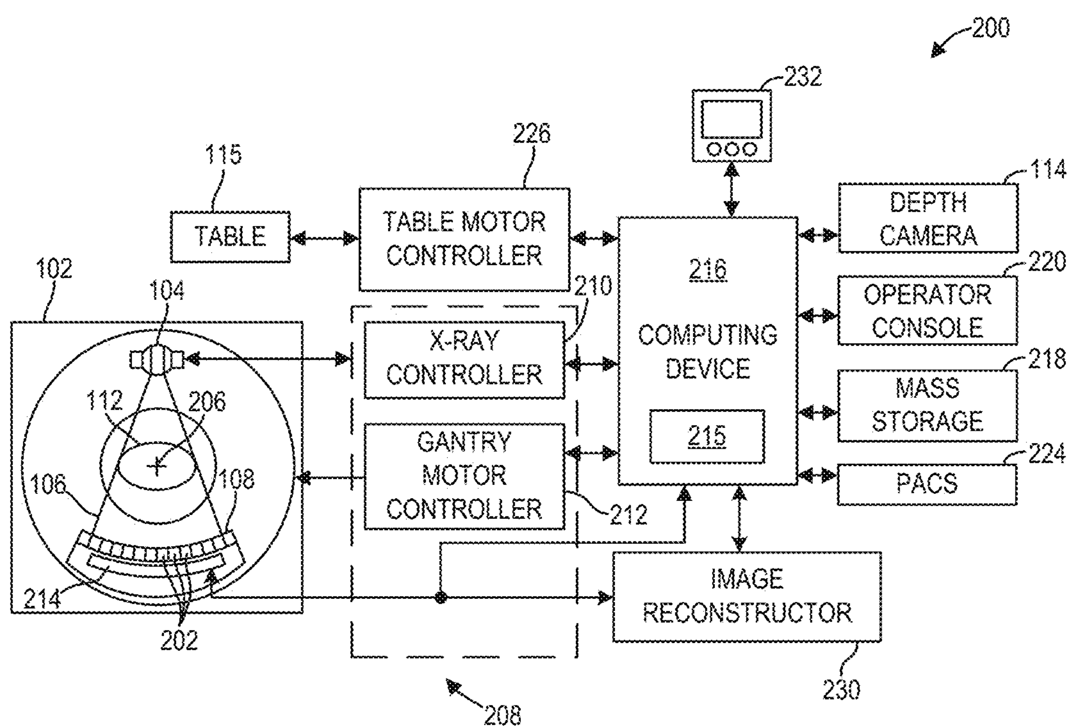
FIG. 2 shows a block schematic diagram of an exemplary imaging system according to an embodiment.
Figure 3:
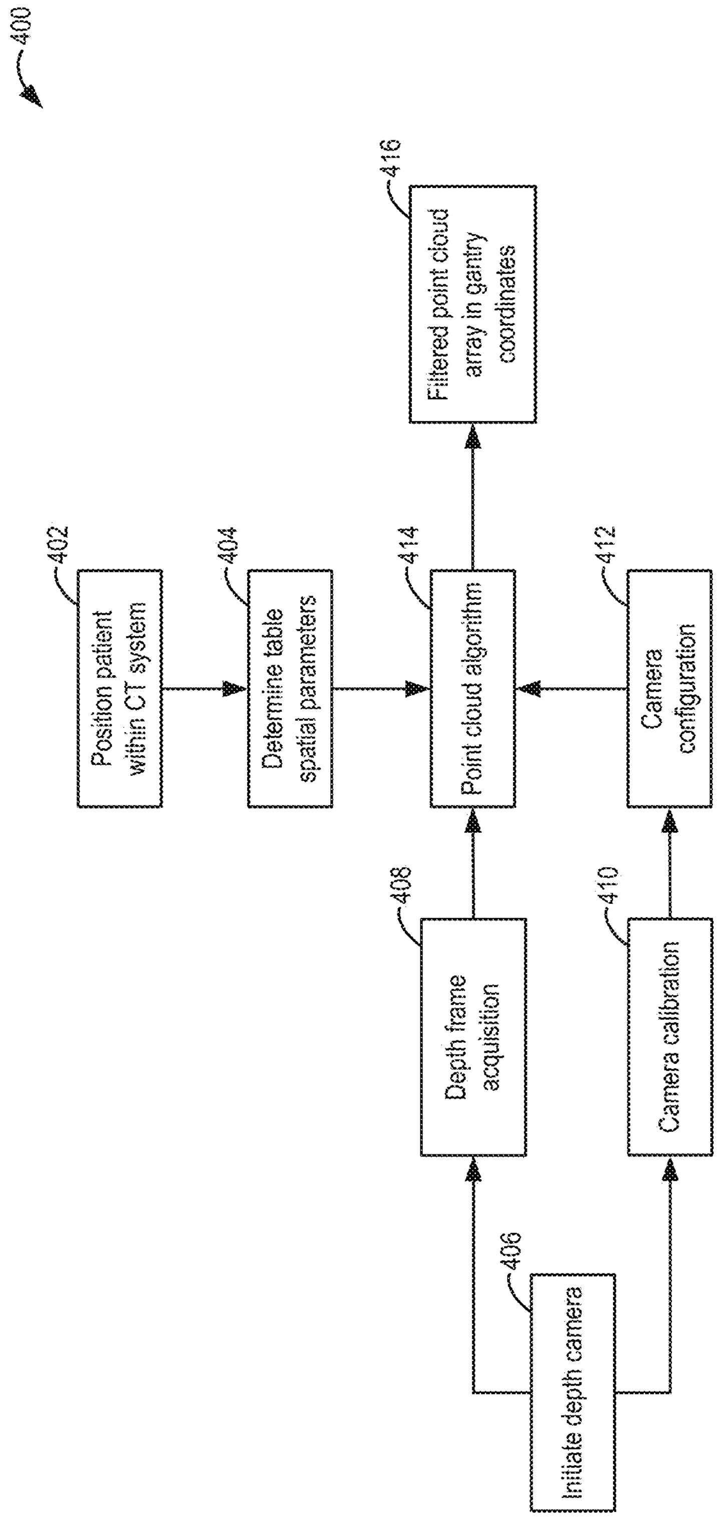
FIG. 3 shows a block diagram of an example algorithm for patient structure estimation prior to imaging according to an embodiment.
Figure 4A:
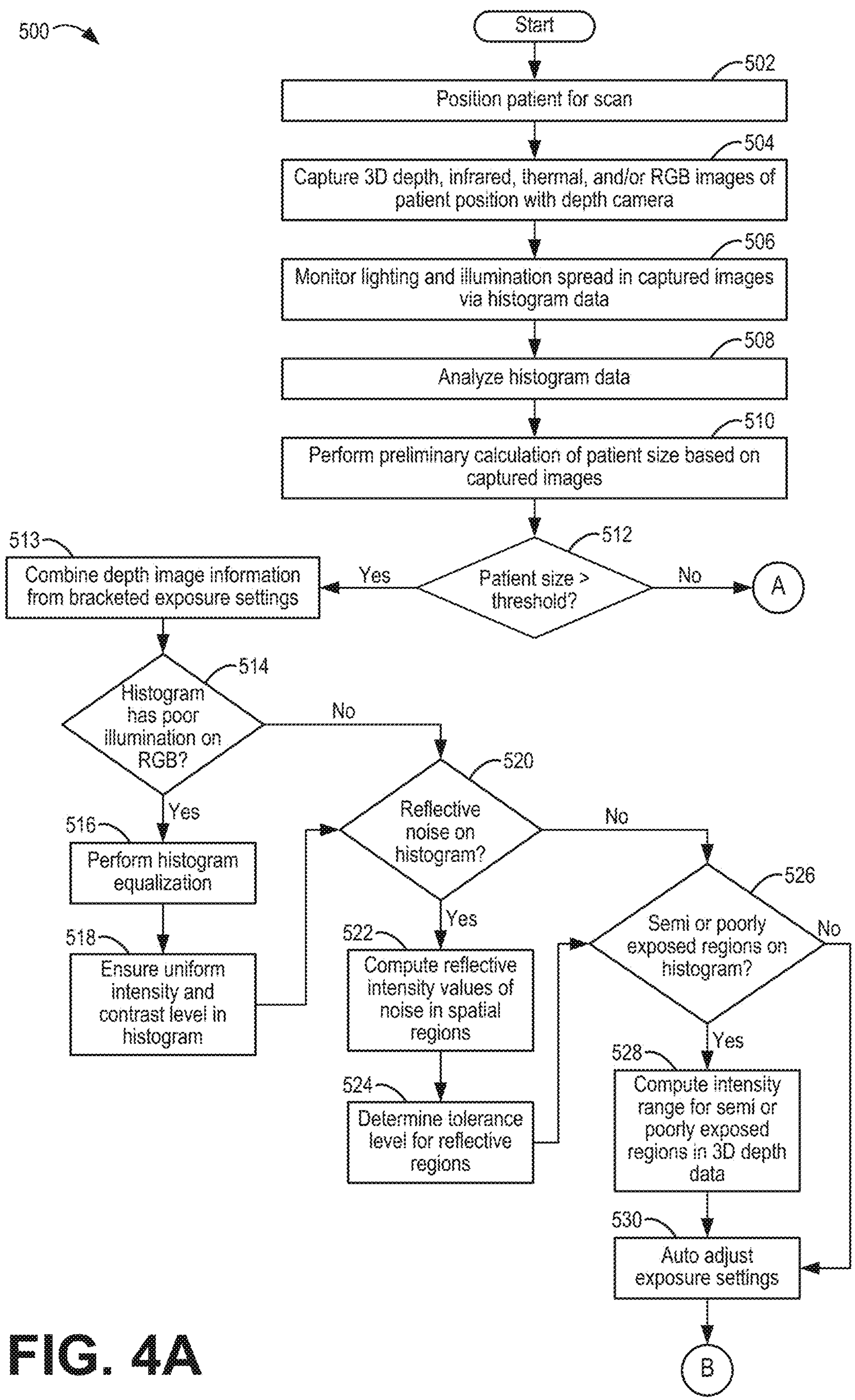
FIGS. 4A-4D show a flow chart illustrating a method for identifying and nullifying effects of variable illumination and reflection on patient structure estimations.
Figure 4B:
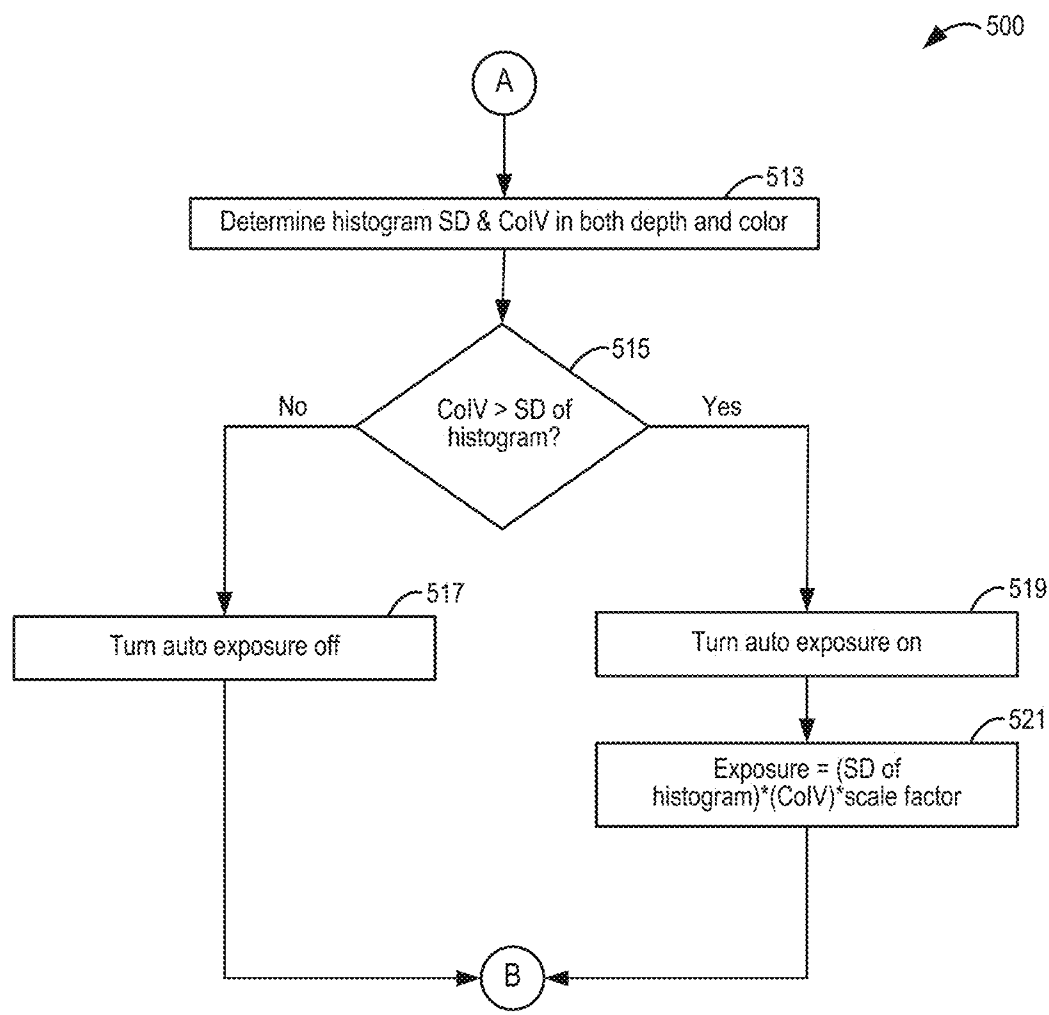
Figure 4C:
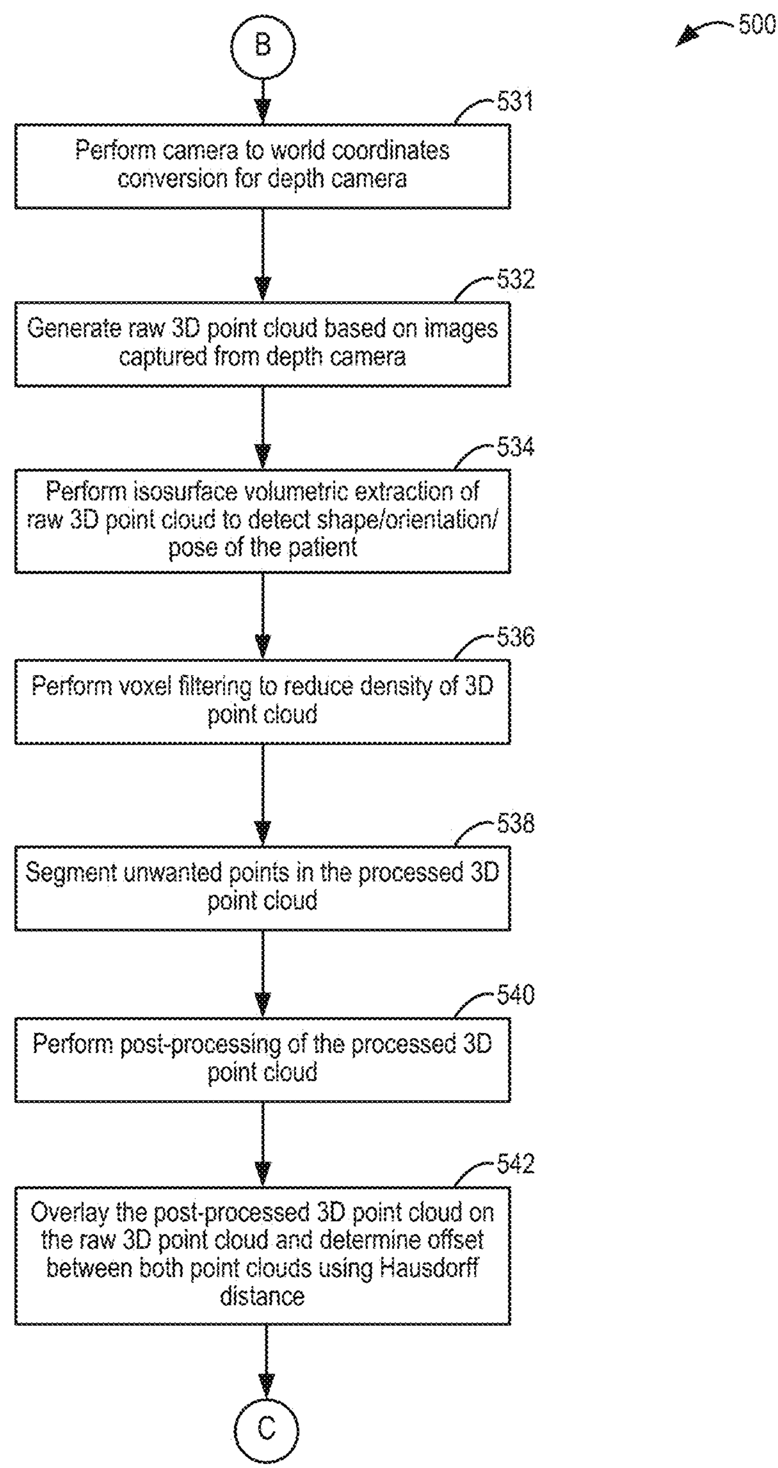
Figure 4D:
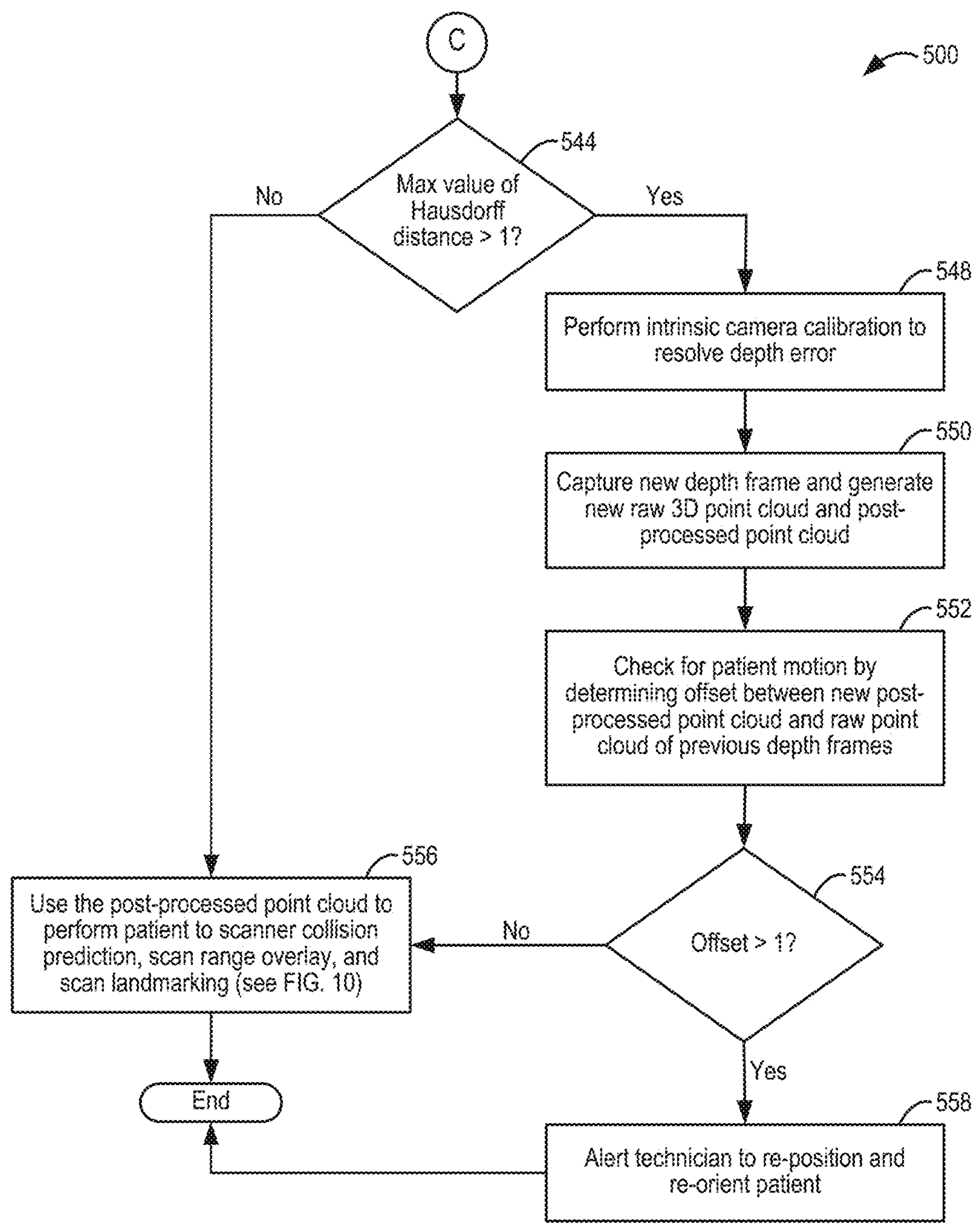
Figure 5:
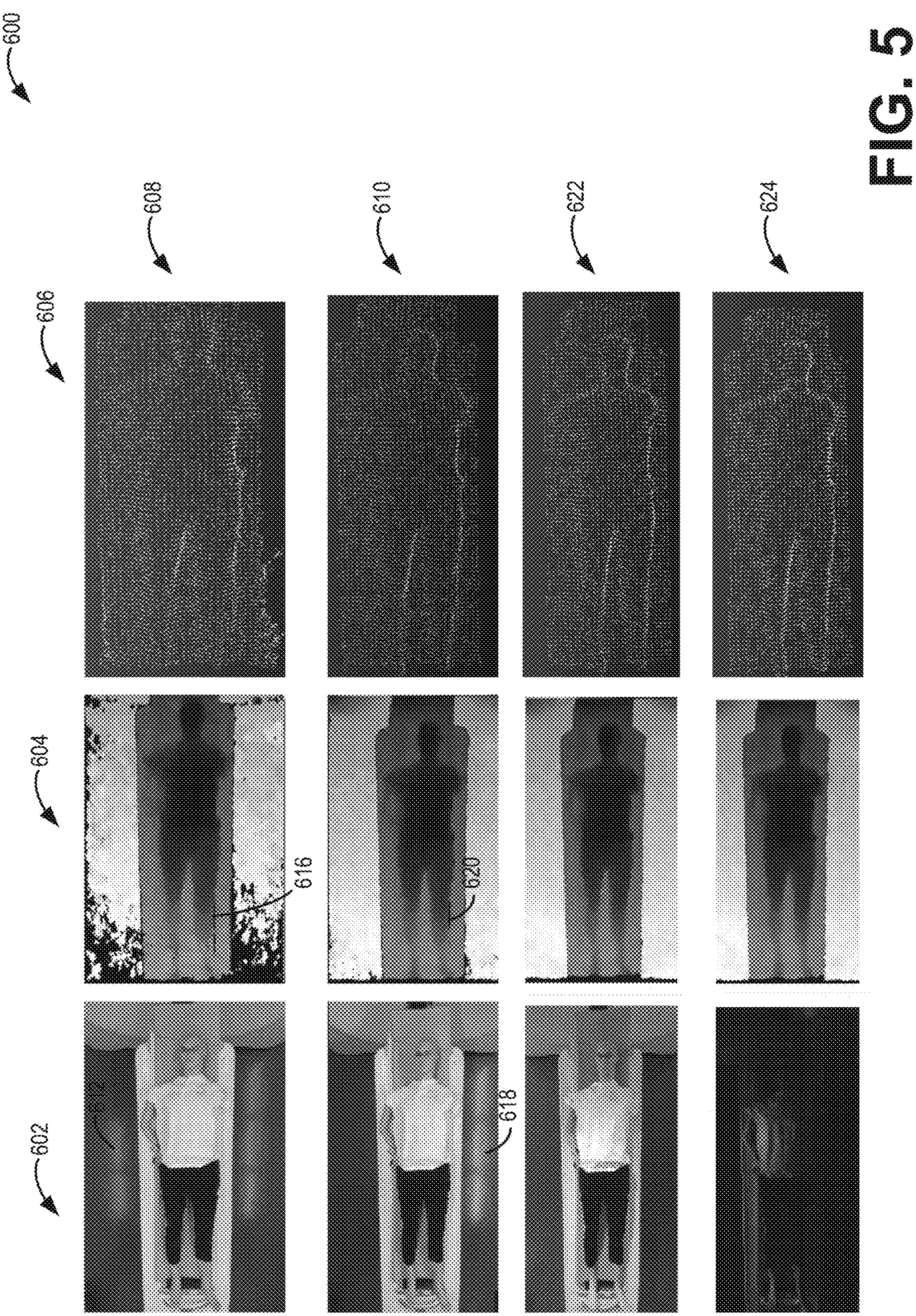
FIG. 5 illustrates various conditions in which the method of FIGS. 4A-4D may generate a filtered point cloud of a patient structure without artifacts resulting from variable illumination and reflection.
Figure 6:
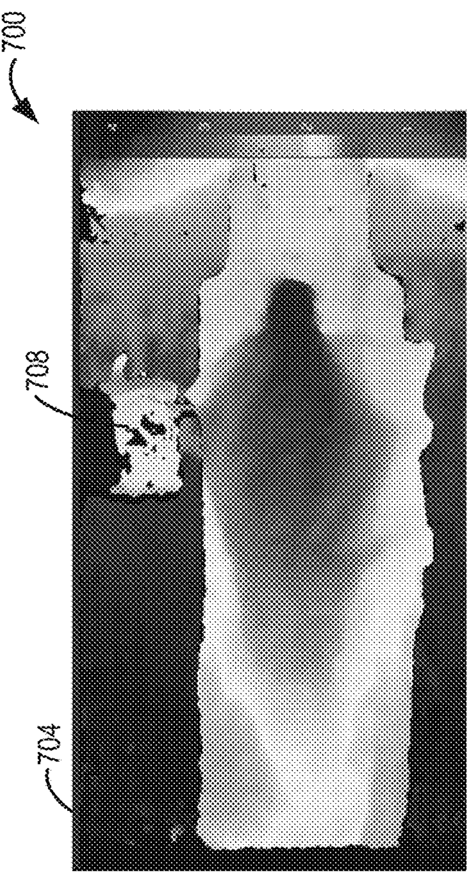
FIG. 6 illustrates an example of point cloud segmentation as described in the method of FIGS. 4A-4D.
Figure 6:
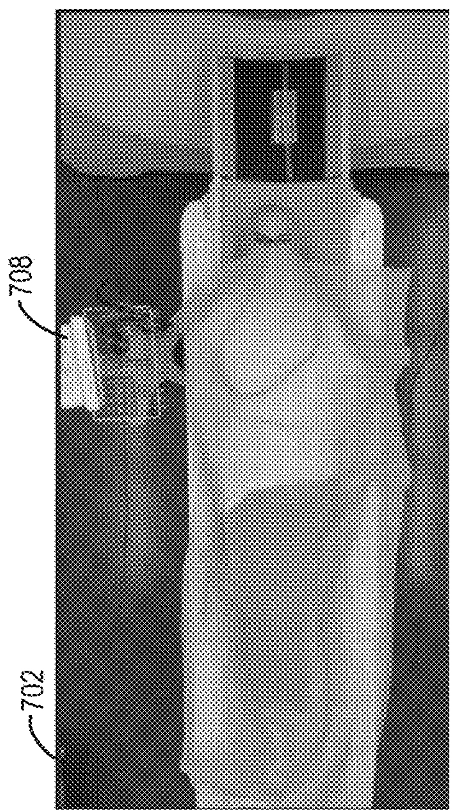
Figure 6:
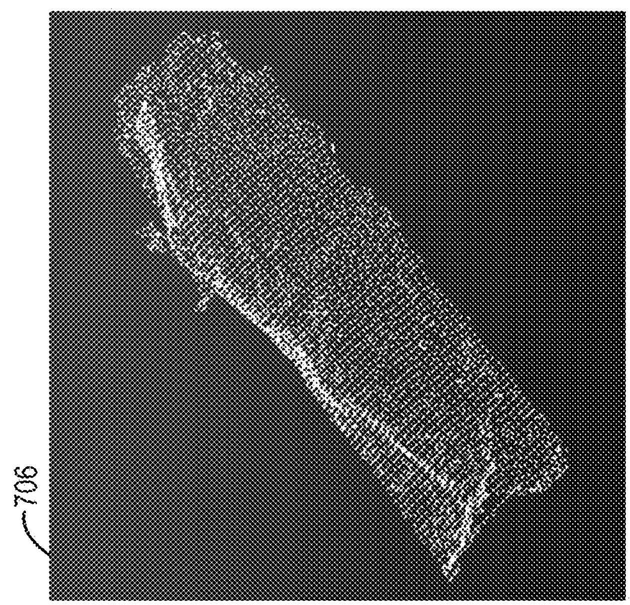
Figure 7:
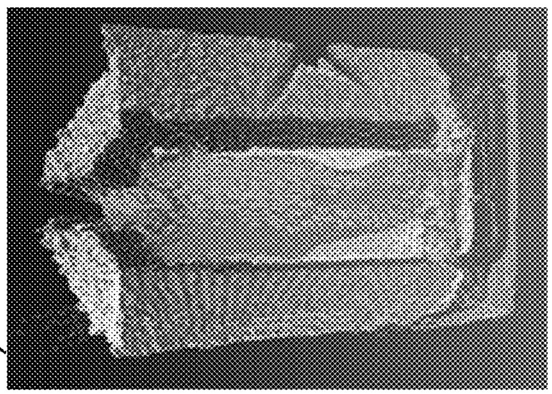
FIG. 7 shows an example of a three-dimensional patient structure estimation under conditions of dim lighting using the method of FIGS. 4A-4D.
Figure 7:
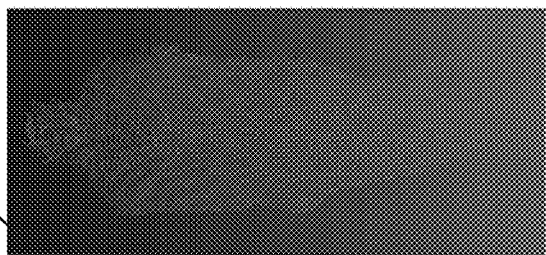
Figure 7:
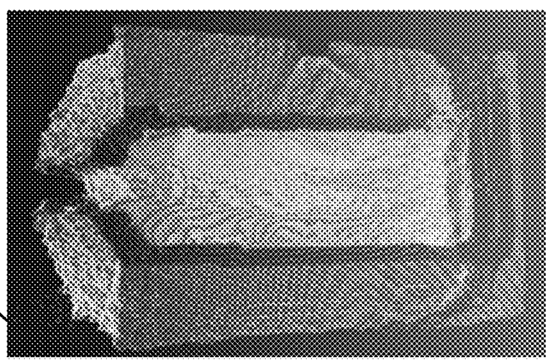
Figure 7:
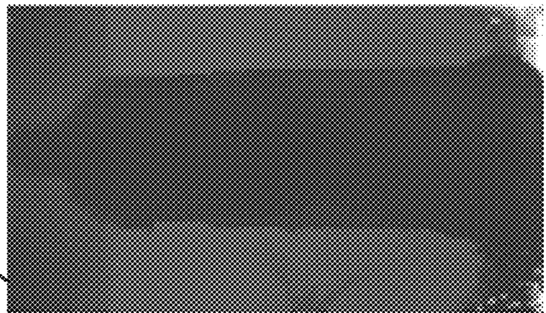
Figure 7:
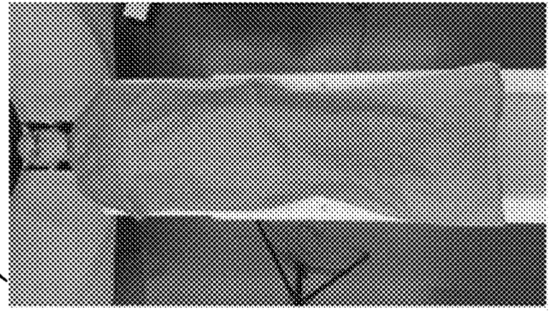
Figure 8A:
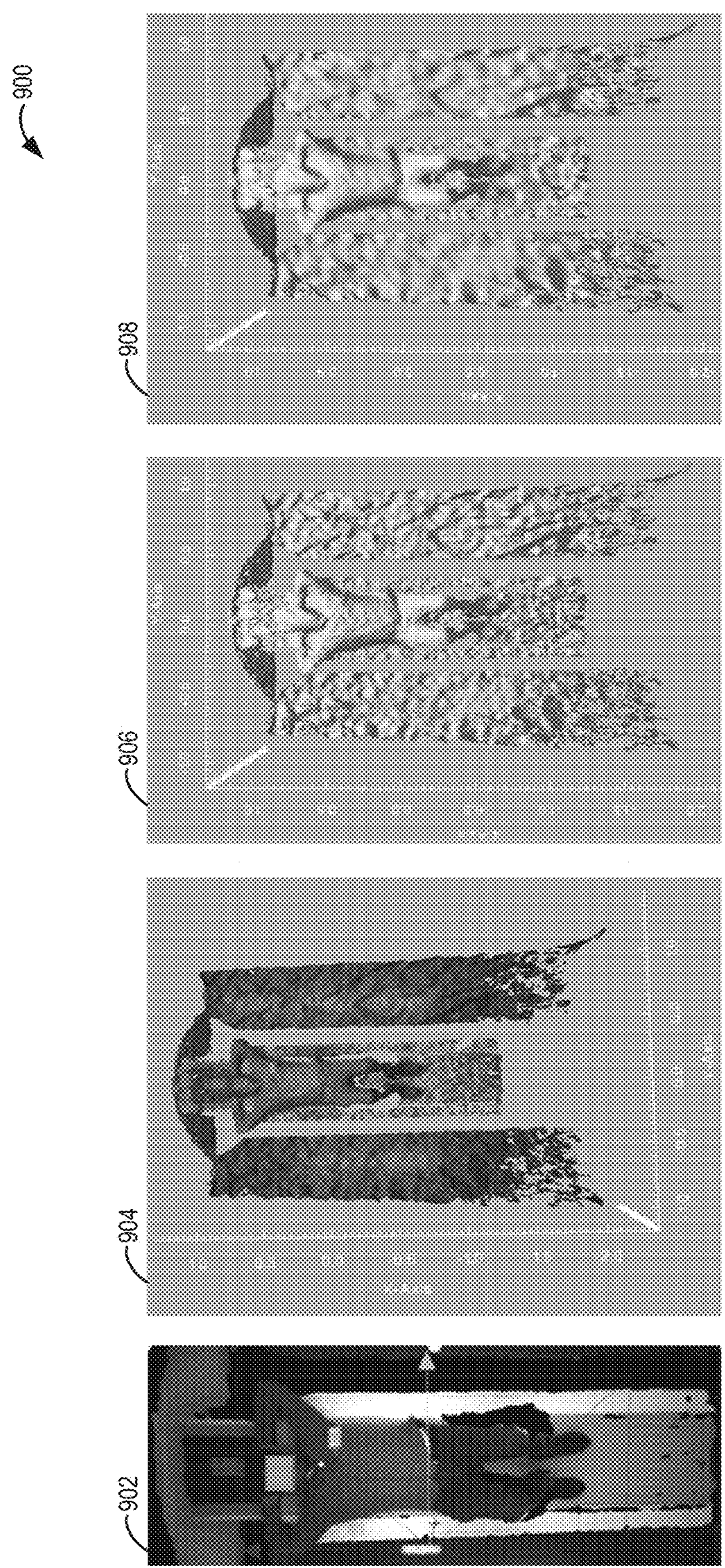
FIGS. 8A-8C illustrate a series of images that may be generated while executing the method of FIGS. 4A-4D.
Figure 8B:
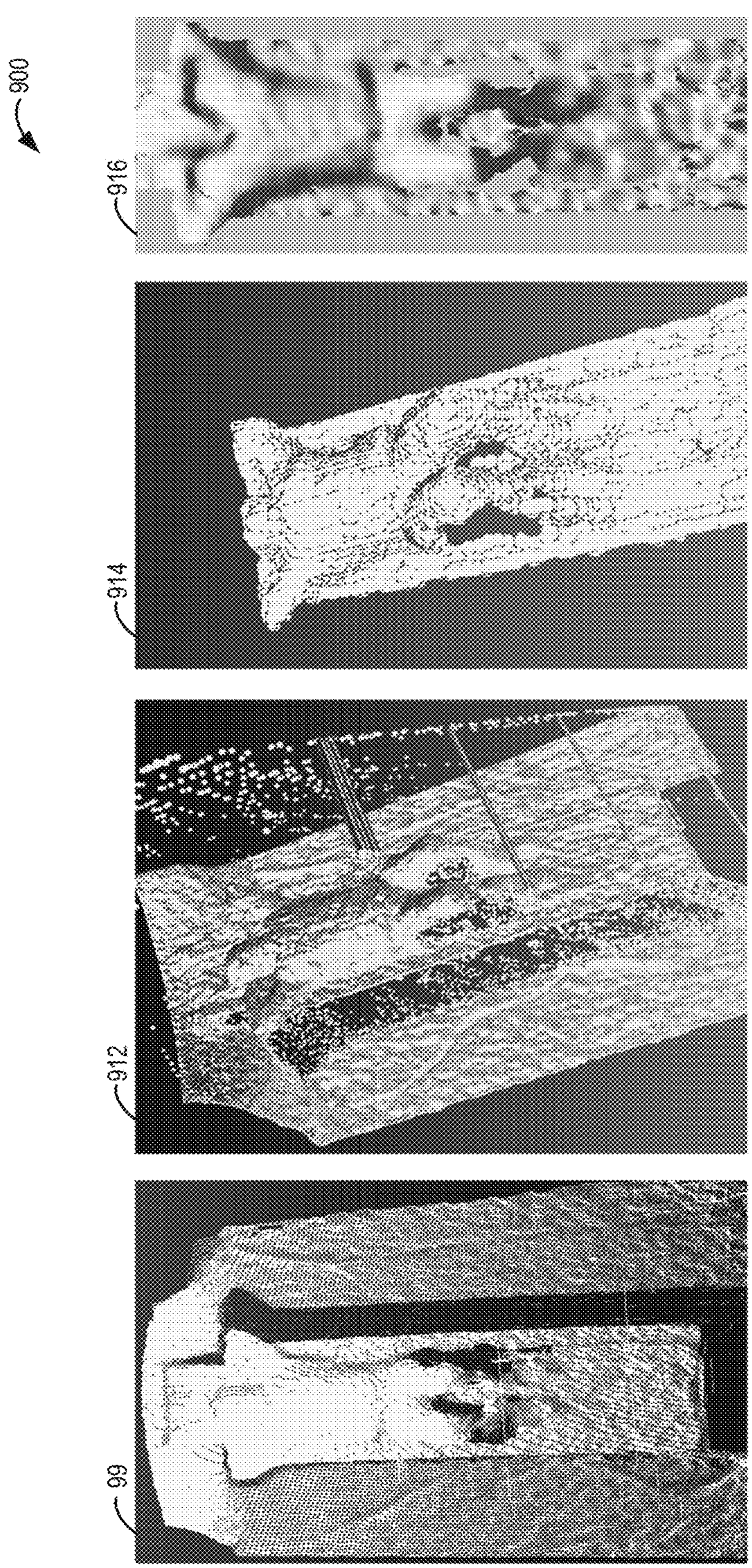
Figure 8C:
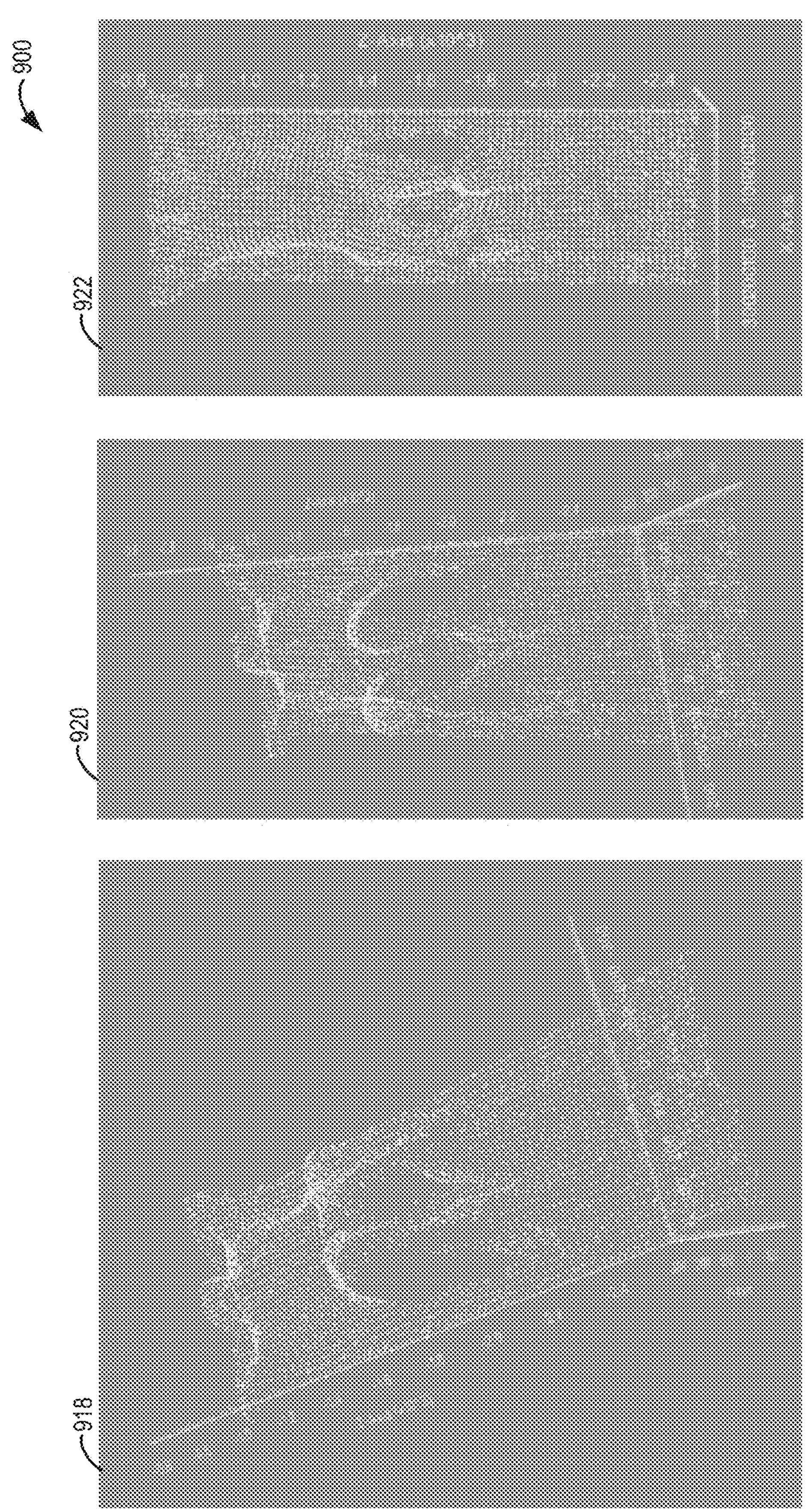

An example of a computed tomography (CT) imaging system that may be used to acquire images in accordance with the present techniques is provided in FIGS. 1 and 2. The CT imaging system of FIGS. 1-2 includes a table positionable within a gantry of the CT imaging system, where the gantry includes an x-ray projector and detector for imaging a subject positioned on the table. The position of the table may be adjusted in order to place the subject at a desired position within the gantry for imaging. Further, the subject may be positioned on the table in a variety of poses and orientations, such as the example poses, in order to attain a desired radiographic image. A high-level overview of an example algorithm that may be used for patient shape estimation prior to imaging is shown in FIG. 3. For example, the algorithm of FIG. 3 may include a method for identifying and nullifying effects of variable illumination and reflection on patient structure estimations, such as the method shown in FIGS. 4A-4D, in order to accurately produce a 3D model of the patient structure for scan outcome prediction and patient pose interpretation, as may be performed using the example method of FIG. 9. FIG. 5 provides examples of variable illumination and exposure conditions in which the method presented in FIGS. 4A-4D may generate an accurate 3D point cloud of a patient structure. FIG. 6 illustrates an example of intelligent segmentation of objects surrounding a patient that may occur during the method shown in FIGS. 4A-4D in order to achieve an accurate 3D patient structure estimation. FIG. 7 provides an example in which the method shown in FIGS. 4A-4D may generate an accurate 3D patient structure estimation under conditions with dim lighting. FIGS. 8A-8C illustrate the method presented in FIGS. 4A-4D as a series of sequential images.

Though a computed tomography (CT) system is described by way of example, it should be understood that the present techniques may also be useful when applied to other medical imaging systems and/or medical imaging devices that utilize a bore and table, such as x-ray imaging systems, magnetic resonance imaging (MRI) systems, positron emission tomography (PET) imaging systems, single-photon emission computed tomography (SPECT) imaging systems, and combinations thereof (e.g., multi-modality imaging systems, such as PET/CT, PET/MR or SPECT/CT imaging systems). The present discussion of a CT imaging modality is provided merely as an example of one suitable imaging modality.

FIG. 1 illustrates an exemplary CT imaging system 100. Particularly, the CT imaging system 100 is configured to image a subject 112 such as a patient, an inanimate object, one or more manufactured parts, industrial components, and/or foreign objects such as implants, stents, and/or contrast agents present within the body. Throughout the disclosure, the terms subject and patient may be used interchangeably, and it is to be understood that a patient is one type of subject that may be imaged by the CT imaging system, and that a subject may include a patient, at least in some examples. In one embodiment, the CT imaging system 100 includes a gantry 102, which in turn may further include at least one x-ray radiation source 104 configured to project a beam of x-ray radiation (or x-rays) 106 (see FIG. 2) for use in imaging the patient. Specifically, the x-ray radiation source 104 is configured to project the x-rays 106 toward a detector array 108 positioned on the opposite side of the gantry 102. Although FIG. 1 depicts only a single x-ray radiation source 104, in certain embodiments, multiple radiation sources may be employed to project a plurality of x-rays 106 towards multiple detectors for acquiring projection data corresponding to the patient at different energy levels.

In some embodiments, the x-ray radiation source 104 projects a fan- or cone-shaped beam of x-rays 106 that is collimated to lie within an x-y plane of a Cartesian coordinate system and is generally referred to as an "imaging plane" or "scan plane." The beam x-rays 106 passes through the subject 112. The beam x-rays 106, after being attenuated by the subject 112, impinges upon the detector array 108. The intensity of the attenuated radiation beam received at the detector array 108 is dependent upon the attenuation of the x-rays 106 by the subject 112. Each detector element of the detector array 108 produces a separate electrical signal that is a measurement of the beam intensity at the detector location. The intensity measurement from all of the detectors is acquired separately to produce a transmission profile.

In third-generation CT imaging systems, the x-ray radiation source 104 and the detector array 108 are rotated with the gantry 102 within the imaging plane and around the subject 112 such that the angle at which the beam of x-rays 106 intersects the subject 112 constantly changes. A complete gantry rotation occurs when the gantry 102 concludes one full 360 degree revolution. A group of x-ray attenuation measurements (e.g., projection data) from the detector array 108 at one gantry angle is referred to as a "view." A view is, therefore, each incremental position of the gantry 102. A "scan" of the subject 112 comprises a set of views made at different gantry angles, or view angles, during one revolution of the x-ray radiation source 104 and detector array 108.

In an axial scan, the projection data is processed to construct an image that corresponds to a two-dimensional slice taken through the subject 112. One method for reconstructing an image from a set of projection data is referred to in the art as a filtered back projection technique. This process converts the attenuation measurements from a scan into integers called "CT numbers" or "Hounsfield units" (HU), which are used to control the brightness of a corresponding pixel on, for example, a cathode ray tube display.

In some examples, the CT imaging system 100 may include a depth camera 114 positioned on or outside the gantry 102. As shown, the depth camera 114 is mounted on a ceiling 116 positioned above the subject 112 and is orientated to image the subject 112 when the subject is at least partially outside the gantry 102. The depth camera 114 may include one or more light sensors, including one or more visible light sensors and/or one or more infrared (IR) light sensors. In some embodiments, the one or more IR sensors may include sensor(s) in both the near IR range and the far IR range, enabling thermal imaging. In some embodiments, the depth camera 114 may further include an IR light source. The light sensor may be any 3D depth sensor, such as a time-of-flight (ToF), stereo, or structured light depth sensor operable to generate 3D depth images, while in other embodiments, the light sensor may be a two-dimensional (2D) sensor operable to generate 2D images. In some such embodiments, the 2D light sensor may be used to infer depth from knowledge of light reflection phenomena to estimate 3D depth. Whether the light sensor is a 3D depth sensor or a 2D sensor, the depth camera 114 may be configured to output a signal encoding an image to a suitable interface, which may be configured to receive the signal encoding the image from the depth camera 114. In other examples, the depth camera 114 may further include other components, such as a microphone to enable the reception and analysis of directional and/or non-directional sounds coming from an observed subject and/or other sources.

In certain embodiments, the CT imaging system 100 further includes an image processing unit 110 configured to reconstruct images of a target volume of the patient using a suitable reconstruction method, such as an iterative or analytic image reconstruction method. For example, the image processing unit 110 may use an analytic image reconstruction approach such as filtered back projection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), model-based iterative reconstruction (MBIR), and so on to reconstruct images of a target volume of the patient.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

CT imaging system 100 further includes a table 115 on which subject 112 is positioned for imaging. The table 115 may be motorized so that the vertical and/or lateral position of the table may be adjusted. Accordingly, the table 115 may include a motor and a motor controller, as will be elaborated below with respect to FIG. 2. The table motor controller moves the table 115 by adjusting the motor for appropriately positioning the subject in the gantry 102 for acquiring projection data corresponding to the target volume of the subject. The table motor controller may adjust both the elevation of table 115 (e.g., the vertical position relative to a ground on which the table sits) and the lateral position of table 115 (e.g., the horizontal position of the table along an axis parallel to a rotational axis of the gantry 102).

FIG. 2 illustrates an exemplary imaging system 200 similar to the CT imaging system 100 of FIG. 1. In one embodiment, the imaging system 200 includes the detector array 108 (see FIG. 1). The detector array 108 further includes a plurality of detector elements 202 that together collect the x-ray beams 106 (see FIG. 1) that pass through the subject 112 to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data. In some examples, the individual detectors or detector elements 202 of the detector array 108 may comprise photon-counting detectors which register the interactions of individual photons into one or more energy bins. It should be appreciated that the methods described herein may also be implemented with energy-integrating detectors.

In certain embodiments, the imaging system 200 is configured to traverse different angular positions around the subject 112 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 112 varies as a function of time, the mounted components may be configured to move along a general curve rather than along a segment of a circle.

In one embodiment, the imaging system 200 includes a control mechanism 208 to control movement of the components, such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary embodiment, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table motor 228 which may adjust a position of the table 115 shown in FIG. 1. Particularly, the table motor controller 226 moves the table 115 via the table motor 228 for appropriately positioning the subject 112 in the gantry 102 for acquiring projection data corresponding to the target volume of the subject 112. For example, the computing device 216 may send commands to the table motor controller 226 instructing the table motor controller 226 to adjust the vertical and/or lateral position of the table 115 via the motor 228.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

As described further herein, the computing device 216 may include computer-readable instructions executable to send commands and/or control parameters to one or more of the DAS 214, the x-ray controller 210, the gantry motor controller 212, and the table motor controller 226 according to an exam imaging protocol that includes clinical task/intent, also referred to herein a clinical intent identifier (CID) of the exam. For example, the CID may inform on the goal of the procedure (e.g., general scanning or lesion detection, anatomy of interest, quality parameters, or other goals) based on a clinical indication, and may further define the desired subject position and orientation (e.g., pose) during the scanning (e.g., supine and feet first). The operator of the system 200 may then position the subject on the table according to subject position and orientation specified by the imaging protocol. Further, the computing device 216 may set and/or adjust various scan parameters (e.g., dose, angle of gantry rotation, kV, mA, attenuation filters) according to the imaging protocol. The imaging protocol may be selected by the operator from among a plurality of imaging protocols stored in memory on the computing device 216 and/or a remote computing device, or the imaging protocol may be selected automatically by the computing device 216 according to received patient information, for example.

During an exam/scanning session, it may be desirable to expose the subject to as low a dose of radiation as possible while still maintaining desired image quality. Additionally, reproducible and consistent imaging quality may be desired from exam to exam and subject to subject, and across different imaging system operators. As such, the imaging system operator may perform manual adjustments to the table position and/or the subject position to center a desired patient anatomy in the center of the bore of the gantry, for example. However, such manual adjustments may be prone to error. Therefore, the CID associated with the selected imaging protocol may be mapped to various subject positioning parameters, including subject pose and orientation, table elevation, an anatomical reference for the scanning, and a start and/or end scan location.

Accordingly, the depth camera 114 may be operatively and/or communicatively coupled to the computing device 216 to provide image data for determining a structure of the subject, including the pose and orientation. Further, the various methods and processes described further herein for determining the patient structure based on the image data generated by the depth camera 114 may be stored as executable instructions in non-transitory memory of computing device 216.

Additionally, in some examples, the computing device 216 may include a camera image data processor 215 that includes instructions for processing information received from the depth camera 114. The information received from the depth camera 114, which may include depth information and/or visible light information, may be processed to determine various subject parameters, such as subject identity, subject size (e.g., height, weight, patient thickness), and current subject position relative to the table and the depth camera 114. For example, prior to imaging, the body contour or structure of the subject 112 may be estimated using an image reconstructed from point cloud data generated by the camera image data processor 215 from images received from the depth camera 114. These subject parameters may be used by the computing device 216, for example, to perform patient-scanner contact prediction, scan range overlay, and scan landmarking, as will be described in more detail herein. Further, data from the depth camera 114 may be displayed via display 232.

In one embodiment, the information from the depth camera 114 may be usable by the camera image data processor 215 to perform tracking of one or more subjects in the field of view of the depth camera 114. In some examples, the image information (e.g., depth information) may be used to perform skeletal tracking, wherein a plurality of joints of the subject are identified and analyzed to determine movement, pose, position, etc., of the subject. The location of the joints during skeletal tracking may be used to determine the subject parameters described above. In other examples, the image information may be directly used to determine the subject parameters described above without skeletal tracking.

Based on these subject positioning parameters, the computing device 216 may output one or more alerts to the operator regarding patient pose/orientation and exam (e.g., scan) outcome prediction, thus reducing the likelihood the subject will be exposed to higher-than-desired radiation dose and increasing the quality and reproducibility of the images generated from the scanning. As an example, the estimated body structure may be used to determine if the subject is in the position for imaging prescribed by a radiologist, thus reducing an occurrence of repeat scanning due to improper positioning. Further, the amount of time the imaging system operator spends positioning the subject may be reduced, allowing for more scans to be performed in a day and/or allowing for additional subject interaction.

A plurality of example patient orientations may be determined based on data received from a depth camera, such as depth camera 114 introduced in FIGS. 1 and 2. For example, a controller (e.g., computing device 216 of FIG. 2) may extract patient structure and pose estimations based on images received from the depth camera, enabling different patient orientations to be distinguished from one another.

A first example patient orientation may include a pediatric patient, and a second example patient orientation may include an adult patient. Both the first example patient orientation and the second example patient orientation may include the patient lying in a supine position in which he/she is lying on his/her back, although the arm positioning differs. For example, the first example patient orientation may include the arms positioned folded above the pediatric patient's head, whereas the second example patient orientation may include the arms positioned folded over the adult patient's abdomen. The supine position, the patient size, and the arm positioning may all be distinguished based on data received from the depth camera and analyzed by methods and algorithms that will be further described herein, such as described with respect to FIGS. 3 and 4A-4D.

As other examples, a third example patient orientation may include a patient covered in a blanket, and a fourth example patient orientation may include a patient wearing a medical gown. Additionally, a fifth example patient orientation may include an operator occlusion. As will be elaborated herein, the inclusion of the blanket in the third example patient orientation, the medical gown in the fourth example patient orientation, and the operator occlusion in the fifth example patient orientation does not affect the patient structure and pose estimations determined based on the data received from the depth camera.

As further examples, the patient to be imaged may be placed in a range of positions. For example, a sixth example patient orientation may include a patient in the supine position, a seventh example patient orientation may include a patient in a prone position in which he/she is lying face down, and an eighth example patient orientation may include a patient in a lateral position in which the patient is lying on one side of his/her body. The supine position, the prone position, and the lateral position (including the side) may all be distinguished from one another based on data received from the depth camera. Thus, there are a variety of poses, orientations, patient shapes/sizes, and potential occlusions (e.g., a blanket, medical gown, operator) from which a 3D patient structure estimation may be determined prior to imaging.

FIG. 3 shows an example algorithm 400 that may be implemented by a controller, such as computing device 216 of FIG. 2, for estimating a patient structure, including a pose and position, prior to radiological imaging based on data received from a depth camera (e.g., depth camera 114 of FIGS. 1 and 2). In the illustrated embodiment, the algorithm 400 is utilized prior to CT imaging; however, it may be understood that embodiments set forth herein may be implemented using other types of medical imaging modalities (e.g., MRI, x-ray, PET, interventional angiography systems). Further, in some embodiments, the patient may be continuously monitored both prior to and during the medical imaging via the algorithm 400 and data received from the depth camera.

In the illustrated embodiment, at 402, the algorithm 400 includes a patient being positioned on a table, such as table 115 of FIG. 1, of a CT imaging system. The patient may be positioned by a technologist according to a prescribed protocol set forth by a radiologist, such as based on a clinical intent identifier (CID) of the exam selected by the radiologist. As one example, the algorithm 400 may guide the technologist in positioning the patient by displaying (e.g., on display 232 of FIG. 2) and/or otherwise communicating the prescribed protocol based on the selected CID. For example, the patient may be positioned in a supine, prone, or lateral position, with head or feet first relative to a gantry of the CT imaging system. The positioning of the patient may be further refined as outlined by the prescribed protocol, such as by adjusting the limb position to achieve a desired pose. Various straps and/or pillows may be used to help the patient maintain the correct position and remain still.

Further, proper positioning of the patient within the CT imaging system means that a patient midline (an imaginary line drawn between the patients eyes to their pubic symphysis) is in the center of the table, and that the table height is adjusted so the center of mass of the region to be scanned may be coincident with the center of rotation of the gantry. Thus, the table parameters may be adjusted. Adjusting the table parameters may include adjusting the table height relative to the gantry so as to avoid any patient collisions with the gantry. Further, the table parameters may be adjusted to ensure the patient will be centered within the gantry once scanning commences.

Once the patient is properly positioned on the scanning table at 402, spatial parameters of the table are determined at 404. For example, a position of four corners of the table within an x-y-z plane of a Cartesian world space coordinate system may be determined. As an illustrative example, a first corner may be positioned at [x1, y1, z1], a second corner may be positioned at [x2, y2, z2], a third corner may be positioned at [x3, y3, z3], and a fourth corner may be positioned at [x4, y4, z4]. In one embodiment, these corners may be defined at as a table top left corner point (e.g., a left side corner of the table closest to the gantry), a table top right corner point (e.g., a right side corner of the table closest to the gantry), a table bottom left corner point (e.g., a left side corner of the table farthest from the gantry), and a table bottom right corner point (e.g., a right side corner of the table farthest from the gantry). For each corner, an x, y, and z value may then be determined. For example, the table bottom left corner point may be located at [−400, −78, −2469], the table top left corner point may be located at [−400, −78, −469], the table bottom right corner point may be located at [400, −78, −2469], and the table top right corner point may be located at [400, −78, −469]. The determined table spatial parameters may be input into a point cloud algorithm at 414, as will be further described below.

At 406, the depth camera, which may be located vertically above the scanning table, is initiated. Initiating the depth camera may include powering "on" the depth camera from an "off" state or from a reduced power mode. Initiating the camera may further include selecting preliminary imaging settings, such as an exposure, focus depth, frame rate, etc. Exposure settings such as the aperture, shutter speed, and ISO may be selected based on scan room conditions (e.g., lighting conditions, reflective surfaces present, etc.). In some examples, the exposure settings may be iteratively adjusted as images are acquired.

At 408, the depth camera acquires depth frames. As one example, the depth camera may illuminate the patient on the scanning table, collectively referred to as a scene, with a modulated light source and observe reflected light using a ToF sensor located within the depth camera. An elapsed duration between the illumination and reflection is measured and translated to distance. The light source may include a solid-state laser or an array of light emitting diodes (LEDs) operating in the near-infrared range (~850 nm), for example, which is invisible to the human eye. An imaging sensor designed to respond to the same wavelength of light emitted by the light source may receive the light and converts the photonic energy to electrical current. The light entering the sensor may have an ambient component and a reflected component, with distance (depth) information only embedded in the reflected component. In ToF sensors, distance is measured for every pixel in a 2D addressable array, resulting in a depth map or a depth frame (e.g., a collection of 3D points, with each point also known as a voxel). As another example, the depth camera may acquire stereo images (e.g., via two or more image sensors that are spaced apart), resulting in a 3D depth frame for each image acquisition. The depth frame may be input into the point cloud algorithm at 414 described below.

At 410, camera calibration of the depth camera 114 is performed. Camera calibration here refers to extracting the intrinsic and extrinsic parameters of the camera using a 2D pattern, such as a checkerboard, so that all data points lie in a plane and the z-component of the data points is zero in world space coordinates. The extrinsic parameters refer to the location and orientation of the camera in the world, whereas the intrinsic parameters refer to the relationships between the pixel coordinates and the camera coordinates. Once the intrinsic and extrinsic parameters are extracted, the matrices are multiplied with a raw point cloud matrix to obtain a camera-to-gantry coordinate transformation. The matrix multiplication may be as follows:

$$\begin{bmatrix} R_{11} & R_{12} & R_{13} \\ R_{21} & R_{22} & R_{23} \\ R_{31} & R_{32} & R_{33} \end{bmatrix} \times \begin{bmatrix} P_X \\ P_Y \\ P_Z \end{bmatrix} \times \begin{bmatrix} F_C & 0 & 0 \\ 0 & C_C & 0 \\ 0 & 0 & 1 \end{bmatrix}$$

with the first matrix representing extrinsic camera parameters, the second matrix representing scene coordinates, and the third matrix representing intrinsic camera parameters. The third or intrinsic matrix may contain two intrinsic parameters that encompass focal length (e.g., $F_c$ and $C_c$).

Once the camera is successfully calibrated, algorithm 400 may continue to 412 where the camera is configured based on the calibration at 410. For example, a scale factor for each of the x- and y-directions, a rotation factor, and a translation factor may be determined based on the camera calibration so that images acquired by the camera are appropriately scaled to world space. For example, the camera configuration may compensate for tilted or rotated depth camera mounting. The camera calibration, including the scale factor(s), rotation factor, and translation factor described above, may also be input into the point cloud algorithm at 414.

At 414, the point cloud algorithm may utilize data input from 404, 408, and 412 to generate a filtered point cloud array in the gantry coordinates, as output at 416. As one example, the point cloud algorithm may render the depth frames acquired at 408 into 3D space as a collection of points, or a point cloud. As another example, additionally or alternatively, the point cloud algorithm at 414 may filter voxel noise and outliers from the depth frame data generated at 408, and the filtered data may then be rendered into a point cloud aligned to the table parameters determined at 404 based on the camera configuration determined at 412. The filtered point cloud array in the gantry coordinates generated by the point cloud algorithm may be output at 416 and may then be used for 3D patient structure estimation to determine proper patient positioning prior to radiological imaging.

Though the use of 3D patient structure estimation prior to radiological imaging has decreased the number of reject and repeat scans as compared to manual patient positioning alone, the use of 3D depth cameras to accurately produce a 3D model of the patient structure is not completely robust. In practice, due to the limitations of the hardware and the structure of the scene, such as depth shadowing and/or the influence of materials with reflection, refraction, or IR absorption, 3D information obtained from depth frames may be insufficient to provide an accurate patient structure estimation. For example, differential lighting and surface reflectivity within radiological scanning rooms may induce holes, or a lack of depth information, in acquired depth frames, as will be elaborated below with respect to FIG. 5. The use of depth frame data containing holes in the generation of a 3D patient structure estimation may lead to an inaccurate or incomplete representation of the patient position and orientation that may be incorrectly interpreted by a technologist as being within the parameters as set forth by the radiologist. Thus, despite the use of a 3D depth camera to aid in proper patient positioning, the patient may still be out of alignment as compared to the prescribed protocol based on the selected CID due to insufficient depth information being used in the generation of the 3D patient structure estimation interpreted by the technologist.

Therefore, FIGS. 4A-4D depict a flow chart illustrating a method 500 for identifying and nullifying effects of variable illumination and reflection on patient structure estimations. Method 500 and the rest of the methods included herein may be executed by computer readable instructions stored in non-transitory memory of a computing device of an imaging system, such as computing device 216 of the imaging system 200 of FIG. 2, which is communicatively coupled to a depth camera, such as depth camera 114 of FIGS. 1 and 2.

Method 500 may begin at 502. At 502, method 500 may include positioning the patient for a scan, as previously described with respect to FIG. 3. For example, the patient may be positioned on a table of a CT imaging system or another radiological imaging system by a technologist based on a CID of the exam selected by the radiologist. The patient may be positioned in a supine, prone, or lateral position with head or feet first relative to a gantry of an imaging system and with limb placement adjusted to a desired pose. Further, the table height (e.g., vertical position) and position may be adjusted to align the patient's center of mass with the center of the gantry for dose optimization during scanning. As one example, the technologist may manually adjust the table height and position by inputting commands to a table motor controller, which may in turn actuate a table motor accordingly. As another example, the computing device may adjust the table height and position by sending commands to the table motor controller to adjust the vertical and/or lateral position of the table the motor based on pre-programmed instructions corresponding to the selected CID. In still other examples, both the technologist and the computing device may adjust the table height and position. For example, the technologist may make coarser adjustments to the table height and position, and then the computing device make refine the table height and position to align the patient's center of mass with the center of the gantry.

At 504, 3D depth, IR, thermal, and/or red, green, and blue (RGB) images of the patient position may be captured using the depth camera. For example, depending on a configuration of the depth camera and the type(s) of sensors included, only one of the 3D depth, IR, thermal, and RGB images may be captured, or more than one of the 3D depth, IR, thermal and RGB images may be captured. By capturing a 3D depth, IR, thermal, and/or RGB (e.g., color) image, distribution information related to patient and table positioning/orientation within the scene may be determined. The distribution information within the captured image may then be graphically summarized and displayed via a histogram. As an example, histogram data for the depth images may be used to identify holes, underexposed and overexposed regions within the depth images, and reflections within the depth images. Additionally or alternatively, histogram data for color images may be used to identify poorly illuminated regions (e.g., dark/bright regions or spots within the image). The histogram data for both color images and depth images may be used alone or in combination to determine optimal values for camera exposure. An example of capturing a depth image of the scene is shown in FIG. 5, as will be described below. An example of capturing a thermal image of the scene is shown in FIG. 6, also described below.

At 506, a lighting and illumination spread in the images captured at 504 may be monitored via histogram data for a determined region of interest (ROI). The ROI contains at least the patient's body and the table the patient is positioned on. The histogram data may provide a graphical representation of a tonal range for images captured at 504 based solely on the intensity of brightness or luminosity for each pixel (e.g., hue is not taken into account) within each image. The tonal range within the histogram may be represented from left to right, with black tones/shades on the left, progressing through midtones in the middle, to highlights on the right. A magnitude or volume of each tone within the tonal range for an image may be represented by a height of individual lines corresponding to each tone or sets of tones present within the captured image. For example, regions of the histogram that are low (e.g., valleys) indicate a low volume of those tones within the image, whereas regions of the histogram that are high (e.g., peaks) indicate a high volume for those tones. As such, the balance and height of peaks in the histogram is an indication of tonal range and tonal balance. Thus, the histogram data may be monitored based on tonal distribution to determine the illumination spread (e.g., overexposure or underexposure) in the images captured at 504.

At 508, the histogram data generated and monitored at 506 may be analyzed to identify poorly illuminated regions, highly reflective regions, and/or poorly or semi-exposed camera regions. For example, if the body of the histogram is skewed to the right, it may indicate the image captured at 504 is overexposed. Alternatively, if the body of the histogram is skewed to the left, it may indicate that the image captured at 504 is underexposed, semi-exposed, or poorly illuminated. Highly reflective regions within the captured image may be represented by an extreme peak or peaks on the right edge within the histogram. In this way, analyzing the histogram data may identify poorly illuminated regions, highly reflective regions, and/or poorly or semi-exposed camera regions.

At 510, a preliminary calculation of patient size is performed based on the captured images. The patient size may include an indication of a thickness of the patient and/or a shape of the patient. In one embodiment, a patient thickness estimation may be determined using depth camera images by applying an algorithm that extracts only the volume of the patient lying on a scan table and multiplying it with a fixed value for density, with color and depth gradients used for patient segmentation (e.g., distinguishing the patient from the scan table to estimate the patient thickness and size).

At 512, it is determined if the patient size is greater than a threshold. The threshold may be a predetermined size threshold used to differentiate between performing two different techniques for minimizing and correcting illumination and reflection variations in the captured images: bracketed exposure depth imaging (BEDI) and a coefficient of illumination variation (CoIV)-based correction. If the patient size is not greater than the threshold (e.g., the patient size is less than the threshold), method 500 proceeds to 513 (see FIG. 4B), and the histogram standard deviation (SD) and the CoIV in both depth and color may be determined. Thus, the CoIV-based correction may be used when the patient is smaller. The CoIV may be a metric to measure the uniformity of illumination within the scene based on the histogram data generated from the image of the scene. The SD of the histogram data may be determined based on the data mean. The CoIV may be defined as the ratio of the SD of all measured illumination values to the mean, or a measure of relative illumination variability. The higher the CoIV, the greater the level of dispersion around the mean. Alternatively, the histogram SD measures the illumination variability proportional the mean, or average, of a histogram data set. In one embodiment, the CoIV may be determined using an algorithm that considers the direction of light illuminating the scene and the discrete pose of the patient, such as:

$$CoIV = \oint_0^t aI(\vec{d} \cdot s) = I \cdot R / (3D \text{ patient location}) \times (\text{pose})$$

where α is an albedo of the surface; I is the intensity of illumination in the direction $\vec{d}$; s is the patient surface normal; the 3D patient location represents the x, y, and z axes of the patient; and the pose may represent eight distinct classes including posterior-anterior (PA), anterior-posterior (AP), left lateral, right lateral, prone, supine, head first, and feet first.

As one example, the histogram data from the depth images and the histogram data from the color images may be combined prior to calculating the CoIV and the SD. As another example, separate CoIV and SD values may be calculated from the depth histogram data and the color histogram data. For example, a first CoIV and a first SD may be determined from the histogram data for the depth images, and a second CoIV and a second SD may be determined from the histogram data for the color images. In some examples, the first CoIV may be combined with the second CoIV and the first SD may be combined with the second SD (e.g., averaged).

At 513, method 500 determines if the calculated CoIV is greater than the SD of the histogram data for both the color images and the depth images. If the CoIV is less than the SD of the histogram data for both the color images and the depth images, it indicates that the data points within the histogram are spread over a large range of values, which may suggest areas exist within the scene with high reflective indices that may induce holes within a 3D depth frame. In contrast, if the CoIV is higher than the SD of the histogram data for both the color images and the depth images, the dispersion of illumination is over a greater range, suggesting the image may be poorly illuminated.

If the CoIV is not greater than the SD of the histogram data for both the depth images and the color images, method 500 continues to 517 and includes turning off auto-exposure. For example, the auto-exposure setting of the depth camera may be turned off to decrease or eliminate image artifacts induced by areas of high reflection within the scene. Once the auto-exposure is turned off, new 3D depth, IR, thermal, or RGB images of the patient position may be captured using the depth camera. Method 500 may then proceed to 531 (see FIG. 4C), as will be described below.

If the CoIV is greater than the SD of the histogram, method 500 may continue to 519, and the depth camera's auto-exposure may be turned on, with the exposure settings determined and applied to capture new images. In particular, the auto-exposure setting may be turned on and may be set based on the CoIV and histogram data, as indicated at 521. In one embodiment, the exposure setting for the auto-exposure may be determined by multiplying the SD of the histogram by the CoIV and a scale factor to aid in extracting noise from the scene. The scale factor refers to a conversion of the physical dimensions of the gantry to corresponding dimensions in the camera image. A gain of the depth camera, which controls amplification of the signal from the camera sensor, may be set to 1/CoIV. Once the auto-exposure is turned on and set based on the CoIV and histogram SD determined at 513, new 3D depth, IR, thermal or RGB images of the patient position may be captured using the depth camera, and method 500 may continue to 531. However, in other embodiments, the CoIV-based correction may be used in combination with BEDI, which will be described below.

Returning to 512 (FIG. 4A), if the patient size is greater than the threshold, method 500 proceeds to 513 and includes combining depth image information from bracketed exposure settings. Thus, when the patient size is greater than the threshold, or optionally in combination with the CoIV-based correction, BEDI may be applied. BEDI seeks to fill any holes contained within depth regions of the captured images using exposure settings ranging from underexposed to overexposed (e.g., exposure settings that bracket the original exposure for an image). For example, a depth image of the scene may be obtained using the most suitable exposure based on current lighting conditions (e.g., depth image N). Next, one overexposed depth image (e.g., relative to exposure settings of depth image N; depth image N+1) and one underexposed depth image (e.g., relative to exposure settings of depth image N; depth image N−1) may be captured. Areas of missing depth information may then be identified by comparing the original depth image with the overexposed and underexposed depth images (e.g., depth image N is compared with depth image N+1 and depth image N−1). Missing depth information in the original depth image (e.g., depth image N) may then be filled using data from the underexposed and/or overexposed images (e.g., depth image N+1 and depth image N−1).

At 514, method 500 includes determining if the histogram has poor illumination on RGB. Various aspects of the histogram may be analyzed, including the illumination on the RGB histogram (e.g., the histogram data from the color images), to determine corrections to apply. If the RGB histogram does not have poor illumination, method 500 may continue to 520, as will be described below.

If the RGB histogram is determined to have poor illumination, method 500 proceeds to 516, and histogram equalization may be performed. The histogram equalization may increase contrast in the captured images by effectively modifying the dynamic range of each image by altering the pixel values, guided by the intensity histogram of that image. As previously described at 506, the histogram is a graphical representation of the intensity distribution of an image, representing the number of pixels for each intensity value considered. For an RGB image, there is a separate table entry for each of the R, G, and B components. Histogram equalization cannot be applied separately to the R, G, and B components, as it may lead to dramatic changes in the image's color balance. Thus, in one embodiment, histogram equalization may be performed by non-linear mapping, which reassigns the intensity values in the input image such that the resultant images contain a uniform distribution of intensities, resulting in a flat (or nearly flat) histogram. This mapping operation may be performed using a lookup table stored in non-transitory memory of the computing device. In another embodiment, a method of RGB histogram equalization that exploits a correlation between color components and is enhanced by a multi-level smoothing technique borrowed from statistical language engineering may be applied. In other embodiments, the RGB image may be first be converted to another color space (e.g., a hue, saturation, and value (HSV) color space or a hue, saturation, and luminance (HSL) color space) before the histogram equalization is performed.

At 518, the RGB histogram processed via histogram equalization at 516 may be analyzed to ensure a uniform intensity and contrast level in the histogram. In one embodiment, an algorithm stored in non-transitory memory of the computing device may determine if the processed histogram is flat (e.g., the pixels are distributed evenly over the whole intensity range). Following equalization, histograms may not be entirely flat due to the character of some intensity values that may exist within the image, though the values may be more evenly distributed. If the processed histogram is determined to not be of uniform intensity and contrast level, the camera exposure settings may be adjusted, a new RGB image captured, and subsequent histogram data equalized to ensure the histogram is flat. Once a processed RGB histogram with a uniform intensity and contrast level has been generated, method 500 may continue to 520.

At 520, method 500 determines if the histogram data for the images captured by the depth camera include reflective noise (e.g., an extreme peak or peaks on the right edge of the graph). If the histogram does not have reflective noise, method 500 may continue to 526, as will be described below. If the histogram data does reveal reflective noise, method 500 continues to 522, and the reflective intensity values of the reflective noise in spatial regions may be computed. In one embodiment, an algorithm stored in non-transitory memory of the computing device may be used to compute the intensity values of pixels corresponding to reflective noise (identified via the histogram) within the spatial regions of the captured image. The spatial regions may include the patient, a hospital gown or blanket being used by the patient, the scan table, the floor surrounding the scan table, medical devices surrounding the scan table, props supporting the patient position on the scan table, and/or any other objects within the captured scene. In another example, additionally or alternatively, the spatial regions may be defined by a grid system and not based on a composition of the region. Once the intensity values for noise/reflective regions within the image have been determined, a tolerance level for these reflective regions may be adjusted at 524. In one embodiment, the tolerance level may be determined through a Euclidean distance. For example, the Euclidean distance may be determined between image points with high reflective noise and surrounding image points to determine and set a reflective tolerance level in which the surrounding image points are not skewed by reflective noise and to ensure reflection saturation (which may induce holes in subsequent 3D depth frame acquisition) does not occur.

At 526, method 500 includes determining if the histogram data for the images captured by the depth camera have semi or poorly exposed regions. Semi or poorly exposed regions may result from dim lighting conditions within the scan room and/or camera exposure settings (e.g., underexposure). For example, an image captured in a scan room with no lighting and with the depth camera's auto-exposure turned off (as further shown with respect to FIG. 7) may result in a poorly exposed image of the scene due to a lack of light during exposure. In other examples, semi or poorly exposed regions may occur as a result of the camera's auto-exposure settings. In other examples, semi or poorly exposed regions may be a result of camera positioning relative to the scene in conjunction with exposure settings and/or lighting conditions within the scan room.

If the histogram data do not have semi or poorly exposed regions, method 500 may continue to 530, as will be described below. If the histogram data does reveal semi or poorly exposed regions (e.g., an extreme peak or peaks on the left side of the graph), method 500 proceeds to 528, and the intensity range for semi or poorly exposed regions in the 3D depth data may be computed. For example, the computing device may identify the semi or poorly exposed regions based on the position of valleys within the histogram data and may further determine the intensity range of those valleys.

At 530, the camera exposure settings may be automatically adjusted. In one embodiment, the exposure settings may be automatically adjusted using a look-up table stored in non-transitory memory of the computing device that is programmed with exposure settings indexed as a function of intensity ranges identified in the histogram data (e.g., such as at 518, 522, and/or 528). In some examples, responsive to no poor illumination, no reflective noise, and no semi or poorly exposed regions on the histogram being identified, the input intensity ranges may result in the same exposure settings being output by the look-up table, as the exposure setting may already be suited to the given lighting conditions. As another example, responsive to identifying poor illumination at 514, such as due to dim lighting conditions, the exposure settings may be adjusted to increase the exposure. As still another example, responsive to identifying reflective noise on the histogram at 520, such as due to bright lighting conditions, the exposure settings may be adjusted to decrease the exposure. Further, in some examples, the exposure settings may additionally or alternatively include exposure bracketing, where a selected exposure setting results in additional images being automatically captured at a lower exposure setting and a higher exposure setting at a same acquisition.

At 531, camera to world coordinates conversion may be performed so that the position of objects within the scene may be described independent of camera position (e.g., based on the position of points [x, y, z] in a world coordinate system). In one embodiment, the transformation from camera to world coordinates may be given by:

$$\begin{bmatrix} X_w \\ Y_w \\ Z_w \end{bmatrix} = R \begin{bmatrix} X_c \\ Y_c \\ Z_c \end{bmatrix} + T$$

where the first matrix is the coordinate point of an object in world coordinates, the second matrix represents the coordinate point of same object in camera coordinates, R is a rotation matrix, and T is a transformation matrix. The extrinsic parameters R and T may be obtained during camera calibration.

At 532, a raw 3D point cloud may be generated using the images captured from the depth camera. The raw 3D point cloud refers to a collection of data points defined by the 3D world coordinate system. In one embodiment, the depth camera may illuminate the scene (e.g., the patient on the scanning table) with a modulated light source and observe the reflected light using a ToF sensor located within the camera to generate the raw 3D point cloud. In another embodiment, the computing device may extract the raw 3D point cloud data from stereo camera images. For example, an algorithm may be applied to a pair of captured stereo images to generate the raw 3D point cloud based on disparities between matching features in the right and left images.

At 534, isosurface volumetric extraction may be performed on the raw 3D point cloud generated at 532 to detect the shape/orientation/pose of the patient. An isosurface is a surface that represents points of a constant value within a volume of space, thus allowing for the 3D patient structure to be extracted from the raw 3D point cloud. This is performed to identify holes or losses of depth information due to underexposure in the depth frames/images. Further, by extracting the raw shape of the patient prior to filtering operations, data pertaining to the patient perimeter and possible patient motion may be detected and used for subsequent filtering at 536. The isosurface may be determined using algorithms stored as executable instructions in the computing device. In one embodiment, an algorithm may use a voxel representation of the volume, considering each data point as the vertex of some geometric primitive, such as a cube or tetrahedron. These primitives, or cells, subdivide the volume and provide a useful abstraction for computing isosurfaces. For example, the isosurface volume may be extracted by converting the depth frames or depth values to a 3D point cloud or mesh model. The frames may be converted to a 3D volumetric isosurface representation with dimensions in the x-, y-, and z-directions using vertex shaders and a marching cubes algorithm to adapt a polygon into 3D point cloud data. This rendering technique will fit and reconstruct the shape of the patient in 3D world coordinates. In another embodiment, the isosurface may be extracted from using an algorithm that combines aspects of both geometric decomposition techniques and span space algorithms.

At 536, voxel filtering may be performed to reduce a density of the 3D point cloud and speed up subsequent computational processes (e.g., generation of a 3D patient structure estimation may occur in less than 100 ms). In one embodiment, a voxel grid filter may be used to return a processed point cloud with a smaller number of points that accurately represent the input point cloud as a whole. The voxel grid filter down-samples the data by taking a spatial average of the points in the cloud, with the sub-sampling rate adjusted by setting the voxel size along each dimension. Any points that lie within the bounds of each voxel are assigned to that voxel and will be combined into one output point (e.g., point clustering). In another embodiment, a pass through filter may be applied to produce the processed point cloud. The pass through filter passes the input points through constraints that remove non-finite points and well as any points that lie outside of a specified field.

At 538, the processed 3D point cloud may be segmented so that only points of interest are maintained within the scene. The points of interest herein including the table and patient body positioned on the table. Segmentation is the process of grouping point clouds into multiple homogeneous regions with similar properties (e.g., labeling each measurement in a point cloud, so that the points belonging to the same surface or region are given the same label). The process of object recognition and classification is the step that labels these regions. Once the objects are extracted and classified, it becomes possible to remove noise and unwanted objects. For example, segmentation in conjunction with object recognition and classification may be used to remove points in the processed 3D point cloud that correlate to equipment surrounding the table, such as a lifesaving apparatus, as described further with respect to FIG. 6. Other objects in the scanning room that may be segmented from the scene may include chairs, benches, shelves, carts, and/or other various medical equipment.

In one embodiment, an edge-based segmentation algorithm may be used to remove noise and unwanted objects from the processed 3D point cloud. Edge-based segmentation algorithms have two main stages: edge detection which outlines the borders of different regions, followed by the grouping of the points inside the boundaries giving the final segments. Edges are defined by the points where changes in the local surface properties exceed a given threshold. In another embodiment, segmentation may be performed by model fitting algorithms that are based on the decomposition of man-made objects into geometric primitives (e.g., planes, cylinders, spheres). For example, the model fitting algorithm may extract shapes by randomly drawing minimal data points to construct candidate shape primitives. The candidate shapes are checked against all points in the dataset to determine a value for the number of the points that represents the best fit.

At 540, post-processing of the processed 3D point cloud may be performed to further refine unwanted points and noise that may negatively impact the 3D patient structure estimation. The parameters for post-processing may be set based on the reflective and non-reflective regions determined at 524 (see FIG. 4A). In one embodiment, post-processing may be performed through supervoxelization, which over-segments the point cloud by grouping the points into homogeneous segments called supervoxels in terms of various attributes (e.g., normals, colors, intensity, shape). The supervoxelization may commence with a normal (regularly spaced) voxelization that groups the points into a 3D grid, and then for each voxel, neighboring points with similar attributes are clustered iteratively such that a supervoxel with an irregular shape is formed. In another embodiment, supervoxelization may be performed in conjunction with Euclidean clustering by using a 3D grid subdivision of the space with fixed width boxes, or more generally, an octree data structure.

At 542, the post-processed 3D point cloud may be overlayed on the raw 3D point cloud and the offset between both point clouds determined using Hausdorff distance. The Hausdorff distance measures an extent to which each point of a model set lies near some point of an image set and vice versa. Thus, this distance can be used to determine a degree of resemblance between two objects that are superimposed on one another. For example, the post-processed point cloud may be viewed as the model set and the raw 3D point cloud generated at 532 may be viewed as the image set, with the offset between the two determined based on the Hausdorff distance using an algorithm stored in the non-transitory memory of the computing device.

At 544 (see FIG. 4D), method 500 determines if the maximum value of the Hausdorff distance determined at 542 is greater than one in any of the x-, y-, and z-directions (e.g., defined by the x, y, and z axes of the patient). The closer the determined Hausdorff distance is to zero, the more the two point clouds resemble each other. Alternatively, if the maximum determined value is greater than one in any of the x-, y- and z-directions, it may indicate a depth error related to depth camera calibration.

Figure 9:
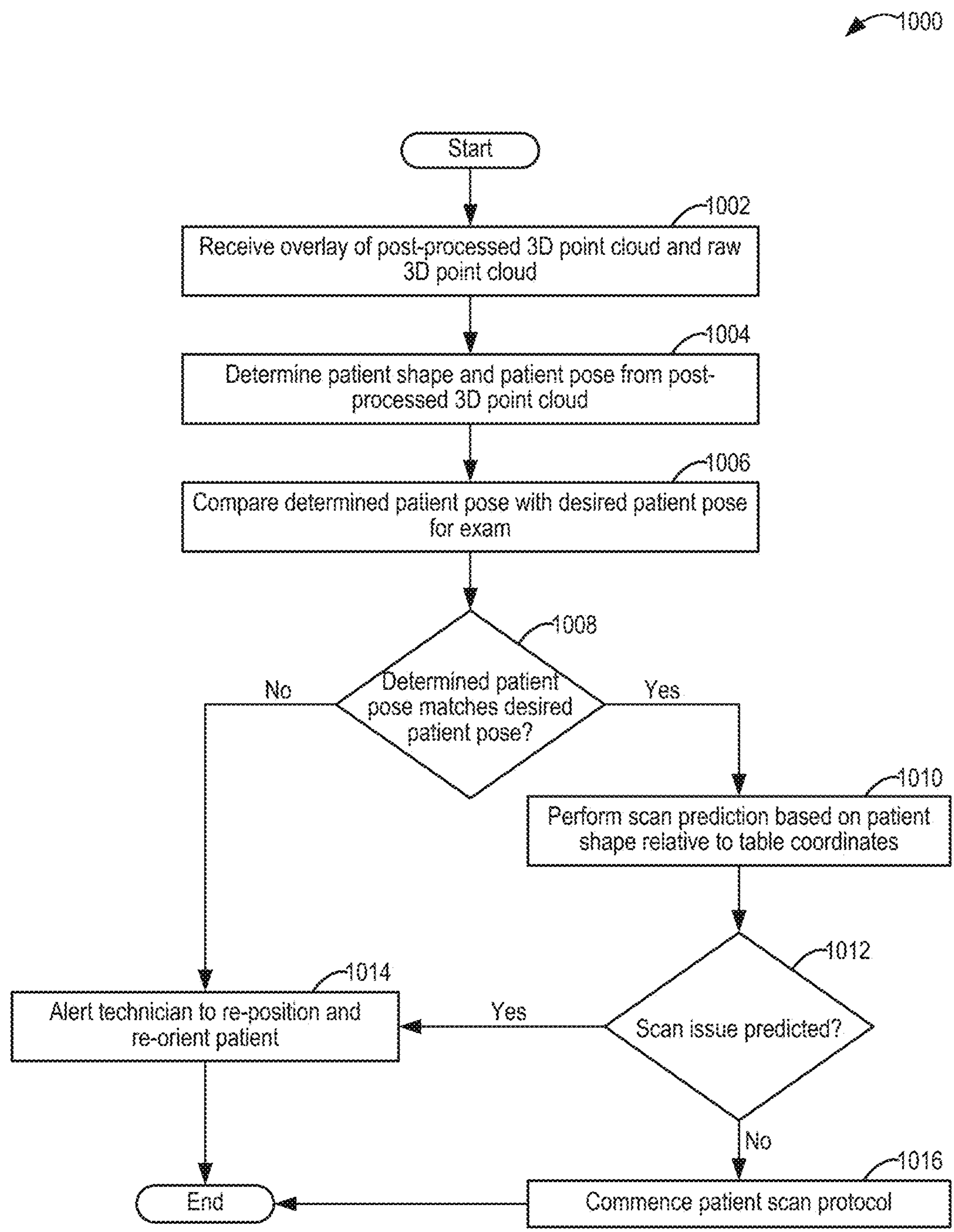
FIG. 9 shows a flow chart illustrating a method for determining if a patient is positioned for a desired exam outcome.

If the Hausdorff distance is not greater than one, method 500 may continue to 556, and the post-processed point cloud may be used to perform scan outcome prediction, scan range overlay, and scan landmarking, as will be further described below with respect to FIG. 9. Method 500 may then end.

If the Hausdorff distance is greater than one, method 500 may continue to 548, where intrinsic camera calibration may be performed to resolve the depth error. Once the depth camera has been recalibrated, method 500 may continue at 550 where a new depth frame may be captured and used to generate a new raw 3D point cloud and post-processed 3D point cloud by repeating the workflow starting at 504.

At 552, method 500 may check for patient motion by determining the offset between the new post-processed 3D point cloud and the raw 3D point cloud of previous depth frames. The offset refers to changes in the patient position that have occurred between acquiring the previous depth frames and the new (e.g., currently acquired) depth frame. The offset may be determined by overlaying the new post-processed 3D point cloud on the raw 3D point cloud (generated at 532 from the first depth frames acquired in method 500) and using the Hausdorff distance as previously described at 542.

At 554, method 500 may determine if the offset determined at 552 is greater than one in either of the x-, y-, and z-directions. If the offset is not greater than one, it may indicate that the patient has not moved, and method 500 may continue to 556, where the post-processed point cloud may be used to perform scan outcome prediction, scan range overlay, and scan landmarking, and method 500 may end.

If the offset is greater than one, it may indicate that patient motion has occurred, and method 500 may continue to 558, where the technician may be alerted to re-position and re-orient the patient. The alert may be a notification issued by the computing device in response to the offset determined at 554 being greater than 1. Method 500 may then end. For example, method 500 may be repeated once the technician has re-positioned and re-oriented the patient to resolve discrepancies related to patient motion/movement.

Implementation of method 500 may allow for the extraction of a 3D point cloud of a patient structure containing a full range of depth information, independent of depth camera exposure settings and lighting conditions within the scan room. FIG. 5 illustrates several example representations 600 of variable scan room conditions from which a depth frame may be captured and subsequently used to generate a 3D point cloud of a patient structure. A 2D image of the patient is shown in a first column 602, a tonal depth image determined from the 2D image is shown in a second column 604, and a 3D point cloud of the patient determined from the tonal depth image is shown in a third column 606. Each row represents data acquired during different lighting conditions. For example, the 2D image, tonal depth image, and 3D point cloud from a first lighting condition are show in a first row 608; the 2D image, tonal depth image, and 3D point cloud for a second lighting condition are shown in a second row 610; the 2D image, tonal depth image, and 3D point cloud for a third lighting condition are shown in a third row 622; and the 2D image, tonal depth image, and 3D point cloud for a fourth lighting condition are shown in a fourth row 624.

The first lighting condition shown in first row 608 includes conditions in which all the lights in the scan room are on (e.g., a bright lighting condition) and the depth camera's auto-exposure is turned on. This results in an areas of high reflection 612 on either side of the patient on the scan table, as shown in the 2D image (first column 602). These areas of high reflection result in a loss of depth information in the tonal depth image, as shown in second column 604 for first row 608. The loss of depth information, or depth holes, can be seen throughout the frame as black regions. These depth holes may lead to an inaccurate patient 3D structure estimation if not corrected. For example, a depth hole 616 can be viewed along the outer left side of the patient's calf in the tonal depth image (second row 604) of first row 608. Using method 500, depth hole 616 may be filled to generate a 3D point cloud containing a full range of depth information pertaining to the patient structure, as shown in 3D point cloud (third column 606) of first row 608.

Similarly, the second lighting condition (second row 610) includes conditions in which the scan room is partially lit and the depth camera's auto-exposure is turned off, resulting in an area of high reflection 618 on the floor to the left side of the patient on the scan table (see the 2D image of first column 602). The area of high reflection 618 may cause a loss of depth information, such as a depth hole 620 to the left outer edge of the patient's knee in the tonal depth image (second row 604) of second column 610. Using method 500 as described with respect to FIGS. 4A-4D, a complete 3D point cloud (third column 606) may still be generated for the second lighting condition (second row 610).

The third lighting condition (third row 622) includes dim lighting in the scan room and the depth camera's auto-exposure is turned on. Because of the dim lighting, areas of high reflection are not present in the 2D image (first row 602). Further, there are no appreciable hopes in the resulting tonal depth image (second row 604). As such, the tonal depth image may undergo reduced correction and processing in generating the 3D point cloud (third column 606) for the third lighting condition (third row 622) compared with the first and second lighting conditions.

The fourth lighting condition (fourth row 624) includes no lighting in the scan room, and the depth camera's auto-exposure is turned off. However, even with the poor lighting, the resulting tonal depth image (second column 604) is free of holes of missing depth information. For example, the histogram of the tonal depth image may be adjusted in order to generate the 3D point cloud shown in third row 606. Thus, method 500 of FIGS. 4A-4D may be used to accurately generate a 3D point cloud of the patient structure under varying lighting conditions and with different depth camera settings by processing the captured images according to features of the captured images themselves (such as poor lighting, high reflection, etc.).

FIG. 6 illustrates an example 700 of how the processed 3D point cloud generated in method 500 may be segmented so that only points of interest are maintained within a scene. As a non-limiting example, a view 702 of the scene shows a medical device 708 surrounding a table on which a patient is positioned. When a thermal image 704 of the scene is captured, object recognition and classification may be used to identify medical device 708 within the thermal image 704. Once medical device 708 has been recognized and classified, it may be segmented, as previously described with respect to FIG. 4C, so that a subsequently generated 3D point cloud 706 only contains information pertaining to the patient orientation, pose, and position on the scan table. For example, 3D point cloud 706 does not show a structure of the medical device 708.

FIG. 7 shows an example 800 of a 3D patient structure determination under conditions of dim lighting using the method presented in FIGS. 4A-4D. Dim lighting conditions may occur when a patient exam scene is partially lit and/or lit using lights with lower intensity. Further, the patient is covered in a blanket, as shown in a 2D image 802. Using method 500 as described with respect to FIGS. 4A-4D, a tonal depth image 804 of the patient covered in the blanket (e.g., in dim lighting conditions) is generated from the 2D image 802 and then used to generate a raw 3D point cloud 806 from which an accurate filtered and processed 3D point cloud 808 may be extracted. The filtered and processed 3D point cloud 808 may then be overlayed onto the raw 3D point cloud 806, as shown an overlay 810. Overlay 810 may then be used to perform patient to scanner collision prediction, scan range overlay, and scan landmarking, as overlay 810 may distinguish the patient structure from the rest of the patient exam scene, including the blanket, a table on which the patient is positioned, and a gantry bore.

FIGS. 8A-8C illustrate various aspects of method 500, as described with respect to FIGS. 4A-4D, as a series of sequential images 900. Image 902 of FIG. 8A is a 2D image of a patient positioned on a scan table that may be acquired at 504 of method 500. Image 904 of FIG. 8A is a depth image of the patient shown in image 902 that may be captured using a depth camera at 532 of method 500. Image 906 of FIG. 8A is a raw 3D point cloud that may be generated and used to perform camera to world coordinate conversion for the depth camera at 531 of method 500. Image 908 of FIG. 8A is a raw 3D point cloud that may be captured of the patient positions at 532 of method 500 following depth camera to world coordinate conversion. Image 910 of FIG. 8B may be generated after performing isosurface volumetric extraction on image 908 at 534 of method 500. Image 912 of FIG. 8B shows image 910 after voxel filtering is performed at 536 of method 500 to reduce the density of the 3D point cloud. Image 914 of FIG. 8B shows image 912 after unwanted regions have been segmented at 538 of method 500. Image 916 of FIG. 8B is a raw 3D point cloud that may be overlayed with the segmented, processed 3D point cloud shown in image 914 to determine potential offset based on patient movement or camera calibration at 542 of method 500. Images 918, 920, and 922 of FIG. 8C show different angles of a post-processed 3D point cloud generated using method 500 that may be used to in the determination of a 3D patient structure estimation prior to medical imaging.

As mentioned above, the 3D patient structure estimation may be used for scan outcome prediction, scan range overlay, and scan landmarking, which may also be used to determine if the patient is in a desired scan pose. Therefore, FIG. 9 provides an example method 1000 for analyzing the 3D patient structure estimation for pose prediction. As one example, method 1000 may be executed by a computing device (e.g., computing device 216 of FIG. 2) as a part of method 500 of FIGS. 4A-4D (e.g., at 556) prior to and/or during medical imaging. A CT imaging system is used by way of example, where the patient is positioned on a table that is movable with respect to a gantry bore.

At 1002, method 1000 includes receiving an overlay of a post-processed 3D point cloud and a raw 3D point cloud. For example, the computing device may use method 500 of FIGS. 4A-4D to iteratively adjust settings of a depth camera and/or correct depth frames determined from images captured by the depth camera until a post-processed 3D point cloud is obtained that does not include holes in the depth information.

At 1004, method 1000 includes determining a patient shape and a patient pose from the post-processed 3D point cloud. In this example, the patient pose includes both a position and orientation of the patient on the table. For example, the post-processed 3D point cloud may be used to determine if the patient is oriented with their head or feet first relative to the gantry and whether the patient is in a supine, prone, or lateral position. Further, the positioning of a patient's limbs may be determined (e.g., arms folded across chest, right leg bent toward chest, left arm straight and elevated, etc.). In one embodiment, the patient shape and the patient pose may be categorized using trained classifiers stored in the non-transitory memory of a computing device to analyze the post-processed 3D point cloud based on anatomical landmarks and body regions. For example, a first classifier may identify the patient orientation (e.g., feet or head first), a second classifier may identify if the patient position (e.g., supine, prone, lateral), a third classifier may identify limb position (e.g., both legs straight, left arm folded across chest), a fourth classifier may estimate the position of internal organs relative to the gantry and scan table (e.g., where the heart is centered with regard to the gantry/scan table), and so on. In another embodiment, the post-processed 3D point cloud may be parsed or segmented by body region (e.g., head, torso) using global constraints (e.g., height, weight, width of the patient) and with the anatomical features within each region further defined based on body boundaries.

At 1006, method 1000 includes comparing the determined patient pose with a desired patient pose. The desired patient pose may be determined based on a received CID of the exam, for example, that dictates a scanning protocol to be used as well as the desired patient pose for performing the exam. As one example, the determined patient pose may be categorized using trained classifiers as previously described and subsequently directly compared with category information outlining the desired patient pose. In such an example, each category of the determined patient pose may be compared to the corresponding category of the desired patient pose, and matches or mismatches may be determined. As another example, additionally or alternatively, model fitting may be used to perform a coarse alignment between the determined patient pose and the desired patient pose. For example, key anatomical landmarks within outlined body segments (e.g., head, torso, pelvis, upper legs, lower legs) determined using trained classifiers may be coarsely aligned with a segmented pictorial structural model of a desired patient pose.

At 1008, method 1000 includes determining if the determined patient pose matches the desired patient pose. As one example, if any category of the determined patient pose does not match the corresponding category of the desired patient pose (e.g., at least one mismatch is present), it may be concluded that the determined patient pose does not match the desired patient pose. Alternatively, if no mismatches are present (e.g., all of the categories between the determined pose and the desired pose match), it may be concluded that the determined patient pose matches the desired patient pose. As another example, additionally or alternatively, an algorithm may analyze the coarse alignment of the determined patient pose and the desired patient pose to determine if the two poses match.

If the determined patient pose does not match the desired patient pose, method 1000 proceeds to 1014 and includes alerting a technician to re-position and re-orient the patient. The technician may be alerted to re-position and re-orient the patient via a notification issued by a computing device, such as computing device 216 of FIG. 2, or a user display (e.g., display 232 of FIG. 2) communicatively coupled to a computing device. For example, the computing device may output an audible or visual alert. The alert may include an indication that the patient pose does not match the desired pose as well as instructions for re-positioning the patient, at least in some examples. Method 1000 may then end.

Returning to 1008, if the determined patient pose does match the desired patient pose, method 1000 proceeds to 1010 and includes performing a scan outcome prediction based on the patient shape relative to table coordinates. The scan outcome prediction may include determining if any potential patient to gantry contact may occur when the patient and scan table are moved into the bore as well as predicting potential contact once scanning commences. In some examples, the scan outcome prediction may further include identifying a starting and ending range of the scan through a scan overlay on the patient shape. In one embodiment, the scan outcome prediction may be performed using an algorithm to determine how many points of the determined patient position exceed a boundary of the bore and how many are within the boundary of the bore using the determined patient structure estimation (e.g., the patient shape and pose) as the input.

At 1012 it is determined if a scan issue is predicted. The scan issue may include a patient position that would result in physical contact between the patient and the gantry bore once scanning commences. The scan issue may additionally or alternatively include the starting and ending range of the scan on the scan overlay not aligning with the CID of the exam. For example, even if the patient is positioned in the correct pose, small adjustments to limb position, for example, may result in clearer images of an anatomy of interest. If a scan issue is predicted, method 1000 proceeds to 1014 and includes alerting the technician to re-position and re-orient the patient, as described above. If a scan issue is not predicted, method 1000 proceeds to 1016 and includes commencing the patient scan protocol. Method 1000 may then end.

In this way, the patient scan may be commenced once the analysis of the patient structure concludes that the patient is properly positioned. The patient structure may be determined using data from a depth camera in which depth holes are compensated for by correcting depth images and/or adjusting the depth camera settings. As a result, an accuracy of patient imaging may be increased while an incidence of reject and repeat scans may be decreased, thereby decreasing an amount of time before a diagnosis can be made. Further, the patient structure may be determined under variable lighting conditions with the same increased accuracy.

The technical effect of applying dynamic corrections to depth images of a patient positioned on a table of a medical imaging system is that an accuracy of a patient pose estimation is increased, thereby increasing an accuracy of a scan by the medical imaging system by ensuring that the patient is in a desired pose for the scan.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical imaging system, comprising:

acquiring depth images of a patient positioned on a table of the medical imaging system via a depth camera;

correcting the depth images based on histogram data from the depth images;

extracting a three-dimensional structure of the patient based on the corrected depth images;

determining a pose of the patient from the extracted three-dimensional structure of the patient;

comparing the determined pose of the patient with a desired patient pose for imaging with the medical imaging system, the desired patient pose defined by a clinical intent identifier for the imaging with the medical imaging system; and outputting a first alert responsive to the determined pose of the patient not matching the desired patient pose.

2. The method of claim 1, wherein the table is movable with respect to a gantry bore, and the method further comprises:

determining a shape of the patient from the extracted three-dimensional structure of the patient;

performing a scan prediction based on the determined shape of the patient relative to coordinates of the table;

outputting a second alert responsive to the scan prediction indicating contact between the patient and the gantry bore, wherein each of the first alert and the second alert is an alert to re-position the patient; and commencing the imaging with the medical imaging system in response to both of the determined pose of the patient matching the desired patient pose and the scan prediction not indicating contact between the patient and the gantry bore.

3. The method of claim 1, wherein correcting the depth images based on the histogram data from the depth images includes performing a coefficient of illumination (CoIV)-based correction and is further based on histogram data from color images of the patient.

4. The method of claim 3, wherein performing the CoIV-based correction includes:

determining a standard deviation of combined histogram data from both the depth images and the color images and a CoIV of the combined histogram data;

turning off an auto-exposure setting of the depth camera responsive to the CoIV of the combined histogram data being greater than the standard deviation of the combined histogram data; and turning on the auto-exposure setting of the depth camera responsive to the CoIV of the combined histogram data not being greater than the standard deviation of the combined histogram data, with the auto-exposure setting adjusted based on the CoIV of the combined histogram data, the standard deviation of the combined histogram data, and a scale factor relating coordinates of the depth images to coordinates of the table.

5. The method of claim 1, wherein correcting the depth images based on the histogram data from the depth images includes performing a bracketed exposure depth imaging (BEDI) correction.

6. The method of claim 5, wherein performing the BEDI correction includes at least one of performing equalization of the histogram data, determining a tolerance level for reflective regions in the depth images, and adjusting exposure settings of the depth camera.

7. The method of claim 6, wherein performing the equalization of the histogram data is responsive to identifying poor illumination in the depth images based on the histogram data, determining the tolerance level for the reflective regions in the depth images is responsive to identifying reflective noise in the depth images based on the histogram data, and adjusting the exposure settings of the depth camera is based on current intensity values of the histogram data and current exposure settings.

8. The method of claim 1, wherein extracting the three-dimensional structure of the patient based on the corrected depth images includes:

generating a three-dimensional point cloud from the corrected depth images; and performing a isosurface volume extraction of the three-dimensional point cloud to extract the three-dimensional structure of the patient.

9. The method of claim 8, wherein the three-dimensional point cloud is a raw three-dimensional point cloud, and the method further comprises:

processing the raw three-dimensional point cloud via voxel filtering and segmentation to isolate the three-dimensional structure of the patient from other objects in the acquired depth images;

overlaying the processed three-dimensional point cloud on the raw three-dimensional point cloud;

determining an offset between the processed three-dimensional point cloud and the raw three-dimensional point cloud using a Hausdorff distance; and responsive to the Hausdorff distance being greater than one, indicating a depth error and adjusting calibration of the depth camera before acquiring new depth images of the patient.

10. A method for a medical imaging system, comprising:

adjusting an exposure mode and gain of a depth camera positioned to acquire images of a patient exam scene based on histogram data from the acquired images;

determining a three-dimensional structure of a patient in the patient exam scene based on the acquired images;

determining a pose of the patient from the determined three-dimensional structure of the patient;

comparing the determined pose of the patient with a desired patient pose comprising a desired position and a desired orientation of the patient defined by a clinical intent identifier; and outputting a first alert responsive to the determined pose of the patient not matching the desired patient pose.

11. The method of claim 10, further comprising:

determining a shape of the patient from the determined three-dimensional structure of the patient;

predicting whether an exam issue will occur based on the determined shape of the patient relative to the patient exam scene; and outputting a second alert responsive to the exam issue being predicted.

12. The method of claim 10, wherein adjusting the exposure mode and the gain of the depth camera includes adjusting the exposure mode between a first mode with auto-exposure on and a second mode with the auto-exposure off based on a distribution of peaks in the histogram data.

13. The method of claim 12, wherein adjusting the exposure mode between the first mode and the second mode based on the distribution of peaks in the histogram data includes:

determining a coefficient of illumination variation (CoIV) and a standard deviation of the distribution of peaks in the histogram data;

responsive to the CoIV being greater than the standard deviation, adjusting the exposure mode to the first mode and setting the gain based on the CoIV; and responsive to the CoIV not being greater than the standard deviation, adjusting the exposure mode to the second mode.

14. The method of claim 10, wherein adjusting the exposure mode and the gain of the depth camera based on the histogram data from the acquired images includes:

determining a tonal range and a tonal balance of each of the acquired images based on the histogram data;

identifying areas of overexposure and underexposure in the acquired images based on intensity values of the tonal range and the tonal balance; and adjusting the exposure mode and the gain based on the intensity values to compensate for the areas of overexposure and underexposure.

15. A system, comprising a rotatable gantry having a bore centrally disposed therein;

a table movable within the bore and configured to position a subject for image data acquisition within the bore;

a camera positioned to acquire images of the subject on the table prior to entering the bore; and a computing device storing executable instructions in non-transitory memory that, when executed, cause the computing device to:

receive images of the subject on the table from the camera prior to the image data acquisition within the bore;

identify a lighting condition in the received images based on histogram data from the received images;

correct the received images based on the identified lighting condition;

identify a pose of the subject on the table based on the corrected images; and output an alert responsive to the pose of the subject deviating from a desired pose for the image data acquisition that is defined by a clinical intent identifier for the image data acquisition.

16. The system of claim 15, wherein the lighting condition includes at least one of dim lighting and bright lighting, and the instructions that cause the computing device to correct the received images based on the identified lighting condition include further instructions stored in non-transitory memory that, when executed, cause the computing device to:

identify underexposed regions in the received images responsive to dim lighting being identified; and identify reflective regions in the received images responsive to bright lighting being identified.

17. The system of claim 16, wherein the computing device includes further instructions stored in non-transitory memory that, when executed, cause the computing device to:

increase an exposure setting of the camera responsive to dim lighting being identified; and correct the underexposed regions in the received images based on new images received from the camera while operating with the increased exposure setting.

18. The system of claim 16, wherein the computing device includes further instructions stored in non-transitory memory that, when executed, cause the computing device to:

decrease an exposure setting of the camera responsive to bright lighting being identified; and correct the reflective regions in the received images based on new images received from the camera while operating with the decreased exposure setting.

19. The system of claim 15, wherein the alert is to re-position the subject, and wherein the instructions that cause the computing device to identify the pose of the subject on the table based on the corrected images include further instructions stored in non-transitory memory that, when executed, cause the computing device to:

generate a three-dimensional point cloud of the subject on the table from the corrected images;

extract a structure of the subject on the table from the three-dimensional point cloud; and compare the structure of the subject on the table to pose classifiers to identify the pose of the subject on the table.

20. The method of claim 1, wherein the desired patient pose comprises a desired position and a desired orientation of the patient, the desired position including one of a supine position, a prone position, and a lateral position of the patient on the table of the medical imaging system and the desired orientation including a desired limb positioning of the patient.

* * * * *